US006255281B1

(12) United States Patent
Pilon et al.

(10) Patent No.: US 6,255,281 B1
(45) Date of Patent: *Jul. 3, 2001

(54) USE OF RECOMBINANT HUMAN UTEROGLOBIN IN TREATMENT OF INFLAMMATORY AND FIBROTIC CONDITIONS

(75) Inventors: Aprile L. Pilon, Gaithersburg; Anil B. Mukherjee, Brookeville; Zhongjian Zhang, Rockville, all of MD (US)

(73) Assignee: Claragen, Inc. and U.S. Government, College Park, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/864,357

(22) Filed: May 28, 1997

(51) Int. Cl.[7] .......................... A61K 38/17; C07K 14/435

(52) U.S. Cl. ............................... 514/12; 514/2; 530/300; 530/836; 530/848; 530/850; 930/250

(58) Field of Search .......................... 514/2, 12; 530/300, 530/836, 848, 850; 930/250

(56) References Cited

U.S. PATENT DOCUMENTS 5,696,092  12/1997  Patierno et al. ...................... 514/21

FOREIGN PATENT DOCUMENTS 617965  10/1994  (EP).

OTHER PUBLICATIONS

Matthews et al., "Crystallization and Characterization of the Recombinant Human Clara Cell 10–kDa Protein", Proteins: Structure, Function and Genetics, 20: 191–196 (1994).
Peri et al., "Expression of Clara Cel 10–kD Gene in the Human Endometrium and Its Relationship to Ovarian Menstrual Cycle," DNA and Cell Biology, 13(5): 495–503 (1994).
Mukherjee et al., "Modulation of Cellular Response to Antigens by Uteroglobin and Transglutaminase" Adv. Exp. Med. Biol., 231:135–152 (1988).
Kikukawa, et al., "Partial Characterization of a Uteroglobin–Like Protein in the Human Uterus and Its Temporal Relationship to Prostaglandin Levels in This Organ", J. Clin. Endo & Met. 67(2): 315–321.
Watts et al., "Effect of dexamethasone therapy on fibronectin and albumin levels in lung secretions of infants with bronchopulmonary dysplasia" J. Pediat. 121: 597–607 (1992).
Rennard et al., "Production of fibronectin by the human alveolar macrophase: Mechanism for the recruitment of fibroblasts to sites of tissue injury in interstitial lung diseases" Proc. Natl. Acad. Sci. USA, 78(11): 7147–7151 (1981).

Lunardi–Iskandar, Y., et al. "Effects of A Urinary Factor from Women in Early Preganancy of HIV I, SID and associated Disease", Nature Medicine, vol. 4, No. 4? 428–434 (1998).
Miele, L. et al., "High Level Bacterial Expression of Uteroglobin, A Dimeric Eukaryotic Protein with Two Interchain Disulfide Bridges, in its natural quaternary Structure" Journal of Biological Chemistry, vol. 265, No. 11: 6427–6435 (1990).
Miele, L., et al., "Uteroglobin: Structure, Molecular Biology, and New Perspectives on Its Function as a Phospholipase $A_2$ Inhibitor" Endocrine Reviews, vol. 8, No. 4: 474–490 (1987).
Kundu, T., et al., "Recombinant Human Uteroglobin Suppresses Cellular Invasiveness Via a Novel Class of High–Affinity Cell Surface Binding Site" Proceedings of the National Academy of Sciences, USA, vol. 93: 2915–2919 (1996).
Levin, S., et al., "Uteroglobin Inhibits Phospholipase $A_2$ Activity", Life Sciences, vol. 38: 1813–1819 (1986).
Miele, L., et al. "Uteroglobin and Uteroglobin–Like Proteins: The Uteroglobin Family of Proteins" Journal of Endocrinology Investigations, vol. 17: 679–692 (1994).
Mantile, G., et al. "Human Clara Cell 10–kDa Protein is the Counterpart of Rabbit Uteroglobin" Journal of Biological Chemistry, vol. 268, No. 27: 20343–20351 (1993).
Manjunath, R. et al. "Inhibition of Thrombin–Induced Platelet Aggregation By Uteroglobin" Biochemical Pharmacology, vol. 36, No. 5–741–746 (1987).
Manjunath, R. et al., "Crosslinking of Uteroglobin By Transglutaminase" Biochemical and Biophysical Research Communications, vol. 121, No. 1: 400–407 (1984).
Dhanireddy, R. et al., "Uteroglobin–Like Protein in Premature Infants: Effect of Gestational Age", Pediatric Research, vol. 23, No. 463A, Abstract No. 1567 (1988).
Dhanireddy, R. et al., "Uteroglobin–Like Protein Levels in Premature Infants on Long Term Venilator Support", Pediatric Research vol. 33, No. 323A, (1993).
Dhanireddy, R. et al., "Detection of a Rabbit Uteroglobin–Like Protein In Human Neonatal Tracheobronchial Washings", Biochemical and Biophysical Research Communications, vol. 152, No. 3: 1447–1554 (1988).
Zhang, Z. et al., "Human Uteroglobin Gene: Structure, Sub–Chromosomal Localization and Polymorphism" DNA and Cell Biology, vol. 16, No. 1: 73–83 (1997).

(List continued on next page.)

Primary Examiner—David Romeu
(74) Attorney, Agent, or Firm—Kramer Levin Naftalis & Frankel LLP

(57) ABSTRACT

Method for treatment of inflammatory and fibrotic conditions in vivo using pure rhUG is disclosed. Method for treating or preventing inflammatory or fibrotic conditions characterized by a deficiency of endogenous functional UG is also disclosed. Compositions containing pure rhUG, optionally also containing lung surfactant, and assay procedures for detection of UG-fibronectin complexes, are also provided.

10 Claims, 7 Drawing Sheets-

OTHER PUBLICATIONS

Vostal, J. et al., "Novel Peptides Derived From a Region of Local Homology Between Uteroglobin and Lipocortin–1 Inhibit Platelet Aggregation and Secretion", Biochemical and Biophysical Research Communications, vol. 165, No. 1: 27–36 (1989).

Volovitz, B. et al., "Relationship Between Leukotriene C4 and a Uteroglobin–Like Protein in Nasal and Tracheobronchial Mucosa of Children" Int. Arch. Allergy Applied Immunology, vol. 86: 420–425 (1988).

Vasanthakumar, G., "Inhibition of Phagocyte Chemotaxis By Uteroglobin, An Inhibitor of Blastocyst Rejection", Biochemical Pharmacology, vol. 37, No. 3: 389–394 (1988).

Perri, A. et al., "Tissue–Specific Expression of the Gene Coating For Human Clara Cell 10–kD Protein, a Phospholipase $A_2$–Inhibitory Protein", Journal of Clinical Investigations, vol. 92: 2099–2109 (1993).

Perri, A. et al., "Uteroglobin Gene Expression In the Rabbit Uterus Throughout Gestation and in the Fetal Lung", Journal of Clinical Investigation, vol. 96: 343–353 (1995).

Mukherjee, A. et al., "Regulation of Extracellular Phospholipase $A_2$ Activity: Implications for Inflammatory Diseases", DNA and Cell Biology, vol. 11, No. 3: 233–243 (1992).

Mukherjee, A. et al., "Phospholipase $A_2$ Enzymes: Regulation and Physiological Role", Biochemical Pharmacology, vol. 48, No. 1: 1–10 (1994).

Miele, L. et al. "Novel Anti–Inflammatory Peptides From the Region of Higher Similarity Between Uteroglobin and Lipocortin I", Nature, vol. 335, No. 6192: 726–730 (1988).

Facchiano, A. et al., "Inhibition of Pancreatic Phospholipase $A_2$ Activity By Uteroglobin and Antiflammin Peptides: Possible Mechanism of Action" Life Sciences, vol. 48: 453–4646 (1991).

Leyton, J. et al., "Recombinant Human Uteroglobin Inhibits the In vitro Invasiveness of Human Metastatic Prostate Tumor Cells and the Release of Arachidonic Acid Stimulated by Fibroblast–Condition Medium" Cancer Research vol. 54: 3696–3699 (1994).

Daly, H. et al. "Bleomycin Induces Strain–Dependent Alterations in the Pattern of Epithelial Cell–Specific Marker Expression in Mouse Lung", Toxicology and Applied Pharmacology, vol. 142:303–310 (1993).

Shijubo, N. et al. "Serum and BAL Clara Cell 10 kDa Protein (CC10) Levels and CC10–Positive Bronchiolar Cells Are Decreased In Smokers", European Respiratory Journal, vol. 10: 1108–1114 (1997).

Aoki, A. et al., "Isolation of Human Uteroglobin from Blood Filtrate", Molecular Human Reproduction, vol. 2, No. 7: 489–497 (1996).

Lesur, O. Clara Cell Protein (CC–16) In Ensurfactint–Associated Protein A (SP–A) an Absestos–Exposed Workers), chest, vol. 109, No. 2: 467–474 (1996).

Barnes, H. et al. "Structural Basis for Calcium Binding By Uteroglobin", Journal of Molecular Biology, vol. 256; 392–404 (1996).

Van Winkle, L. et al., "Repair of Naphthalene–Injured Microdissected Airways In vitro" American Journal of Respiratory Cell and Molecular Biology, vol. 15: 1–8 (1996).

Wuenschell, C. et al., "Embryonic Mouse Lung Epithelial Progenitor Cells Co–Express Immunohistochemical Markers of Diverse Mature Cell Lineages", The Journal of Histochemistry and Cytochemistry, vol. 44, No. 2: 113–123 (1996).

Zhang, Q. et al., "Cross–linking of the $NH_2$–Terminal Region of Fibronectin to Molecules of Large Apparent Molecular Mass", The Journal of Biological Chemistry vol. 271, No. 52: 33284–33292 (1996).

Lesur, O. et al. "Clara Cell Protein (CC–16) Induces a Phospholipase $A_2$–Mediated in Addition of Fibroblast Migration In vitro" American Journal of Respiratory Critical Care Medicine vol. 152: 290–297 (1995).

Dierynck, I. et al., "Potent Inhibition of Both Human Interferon–γ Production and Biologic Activity By the Clara Cell Protein CC–16", American Journal of Respiratory Cell Molecular Biology, vol. 12: 205–210 (1995).

Nord, M. et al., "Calcium–Dependent Binding of Uteroglobin (PCB–BP/CCSP) Two Negatively Charged Fossil Liposomes" EFEBS Letters vol. 374: 403–406 (1995).

Glaser, K.B., "Regulation of Phospholipase $A_2$ Enzymes: Selected Inhibitors and Their Pharmacological Potential", in Advances In Pharmacology, vol. 32 Academic Press Incorporated, pp. 31–66 (1995).

Hard, P. et al., "Solution Structure Of A Mammalian PCB–Binding Protein In A Complex With a PCB", Nature Structural Biology, vol. 2, No. 11: 983–989 (1995).

Stripp, B. et al. "Plasticity of Airway Cell Proliferation and Gene Expression After Acute Naphthalene Injury", American Journal of Physiology, vol. 269: L791–L799 (1995).

Stripp, B. et al., "Clara Cell Secretory Protein: A Determinant of PCB Bioaccumulation In Mammals", American Journal of Physiology, vol. 271: L656–L664 (1996).

Umland, T. et al. "Twixt Form and Function" Nature Structural Biology, vol. 2, No. 11: 919–922 (1995).

Jorens, P. et al. "Potential Role of Clara Cell Protein, An Endogenous Phospholipase $A_2$ Inhibitor, In Acute Long Injury" European Respiratory Journal, vol. 8: 1647–1653 (1995).

Nomori, H. "Protein I (Clara Cell) Serum Levels in Healthy Subjects in Patience With Bacterial Pneumonia" American Journal of Respiratory Critial Care Medicine, vol. 152: 746–750 (1995).

Wu, C., et al. "Integrin Activation and Cytoskeletal Interaction Are Essential for the Assembly of a Fibronectin Matrix", Cell, vol. 83: 715–724 (1995).

Groneck, P. et al. "Association of Pulmonary Inflammation and Increased Microvascular Permeability During the Development of Bronchopulmonary Dysplasia: A Sequential Analysis of Inflammatory Mediators in Respiratory Fluids of High–Risk Preterm Neonates", Pediatrics, vol. 93 No. 5: 712–718 (1994).

Lloret, S. et al., "Effect of Nonapeptide Fragments of Uteroglobin and Lipocortin I on Oedema and Mast Cell Degranulation", European Journal of Pharmacology vol. 264: 379–384 (1994).

Nomori, H., et al. "Protein 1 and Clara Cell 10–kDa Protein Distribution in Normal and Neoplastic Tissued with Emphasis on the Respiratory System", Virchows Archives, vol. 424: 517–523 (1994).

Stripp, B. et al. "Structure and Regulation of the Murine Clara Cell Secretory Protein Gene", Genomics vol. 20: 27–35 (1994).

Umland, T. et al. "Structure of a Human Clara Cell Phospholipid–Binding Protein–Ligand Complex at 1.9 Å Resolution", Nature Structural Biology, vol. 1: 538–545 (1994).

Zhang, Q., et al., "Modulation of Cell Surface Fibronectin Assembly Sites by Lysophosphatidic Acid", Journal of Cell Biology, vol. 127 No. 5: 1447–1459 (1994).

Ray, M. et al. "Cloning and Characterization of the Mouse Clara Cell Specific 10 kDa Protein Gene Comparison of the 5'–Flanking Region With the Human Rat and Rabbit Gene", Biochemical and Biophysical Research Communications, vol. 197, No. 1: 163–171 (1993).

Singh, G. et al. "Mouse Clara Cell 10–kDa (CC10) Protein: cDNA Nucleotide Sequence and Molecular Basis for the Variation of Progesterone Binding of CC10 from Different Species", Experimental Lung Research vol. 19: 67–75 (1993).

Fung, T–C., et al., "Surfactant: Coming of Age for the Treatment of RDA", The Journal of Respiratory Diseases, vol. 13, No. 4: 609–617 (1992).

Okutani, R. et al., "Simple and High–Yield Purification of Urine Protein 1 Using Immunoaffinity Chromatography: Evidence for the Identity of Urine Protein 1 and Human Clara Cell 10–Kilodalton Protein", Journal of Chromatography, vol. 577: 25–35 (1992).

Badcock, N.R. et al., "False–Positive EMIT®–st™ Ethanol Screen with Post–Mortem Infant Plasma", Clinical Chemistry, vol. 38, No. 3: 434–435 (1992).

Stripp, B. et al., "cis–Acting Elements That Confer Lung Epithelial Cell Expression of the $CC_{10}$ Gene", Journal of Biological Chemistry, vol. 267, No. 21: 14703–14712 (1992).

Edelson, J. et al. "Acute Lung Injury Induced by Phospholipase $A_2$: Structural and Functional Changes", American Reviews in Respiratory Diseases, vol. 143: 1102–1109 (1991).

Chan, C–C., et al. "AntiFlammins: Inhibition of Endotoxin—Induced Uveities in Lewis Rats", Ocular Immunology Today, U.Sui, M., et al., editors, Elsevier Science Publishers (Biomedical Division), pp. 467–470 (1990).

Ialenti, A., et al. "Anti–inflammatory Effects of Vasocortin and Nonapeptide Fragments of Uteroglobin and Lipocortin 1 (Antiflammins)", Agents and Actions, vol. 29: 1–2 (1990).

Singh, G. et al., "Clara Cell 10 kDa protein (CC10): Comparison of Structure and Function to Uteroglobin", Biochimica et Biophysica Acta, 1039:348–355 (1990).

Robinson, D., "Macromolecular Transport in Rabbit Blastocysts: Evidence for a Specific Uteroglobin Transport System", Molecular and Cellular Endocrinology, 63: 227–237 (1989).

Scheuer, W., "Phospholipase $A_2$—Regulation and Inhibiton", Wochenschr 67: 153–159 (1989).

Peter, W., "Recombinant Rabbit Uteroglobin Expressed at High Levels in *E. coli* Forms Stable Dimers and Binds Progesterone", Protein Engineering, vol. 3: 66–66 (1989).

Piomelli, D., "Arachidonic Acid in Cell Signaling", Current Opinion in Cell Biology, 5: 274–180 (1993).

van Binsbergen, J. et al., "Synthetic Peptide from Lipocortin I has no Phospholipase $A_2$ Inhibitory Activity", Published by Elsevier Science Publishers B.V. (Biomedical Division), vol. 247, No. 2, 293–297 (1989).

Jackson, P. et al., "Purification and Partial Amino Acid Sequence of Human Urine Protein 1", Journal of Chromatograph, 452: 359–367 (1988).

Ruoslahti, E., "Fibroectin and Its Receptors", Ann. Rev. Biochem., 57:375–413 (1988).

Singh, G., "Identification, Cellular Localization, Isolation and Characterization of Human Clara Cell–Specific 10 KD Protein", The Journal of Histochemistry and Cytochemistry, vol. 36, No. 1, pp. 73–80 (1988).

Singh, G., et al., "Isolation and Amino Acid Composition of the Isotypes of a Rat Clara Cell Specific Protein", Experimental Lung Research, 13:299–309 (1987).

Stenmark, K. et al., "Potential Role of Eicosanoids and PAF in the Pathophysiology of Bronchopulmonary Dysplasia", Am Rev Respir Dis. 136: 770–772 (1987).

Gerdes, J., et al., "Tracheal Lavage and Plasma Fibronectin: Relationship to Respiratory Distress Syndrome and Development of Bronchopulmonary Dysplasia", The Journal of Pediatrics, pp. 601–606 (1986).

Vadas, P. et al. "Potential Therapeutic Efficacy of Inhibitors of Human Phospholipase $A_2$ in Septic Shock", Agents and Actions, vol. 19: 3–4 (1986).

Bitterman, P. et al., "Role of Fibronectin as a Growth Factor for Fibroblasts", The Journal of Cell Biology, 97: 1925–1932 (1983).

Krishnan, R., "'Blastokinin': Inducer and Regulator of Blastocyst Development in the Rabbit Uterus", Science, vol. 158:490–492 (1967).

Jorens et al. "Potential Role of Clara cell protein, an endogenous phospholipase $A_2$ inhibitor, in acute lung injury," Eur. Resp. J. 8: 1647–1653 (1995).

Itoh et al. "Protein 1: Its Purification and Application in Clinical Medicine" J. Clin. Lab. Anal. 7: 394–400 (1993).

Federal Register, published Aug. 16, 1994.

Abman et al, "Pathophysiology and Treatment of Bronchopulmonary Dysplasia: Current Issues," Pediatric Clinics of North America, vol. 41, No. 2, pp. 277–315 (1994).

Akiyama et al, "Fibronectin and integrins in invasion . . . ," Cancer and Metastasis Reviews, vol. 14, pp. 173–189 (1995).

Andersson et al, "Heterologous Expression of Human Uteroglobin/Polychlorinated Biphenyl–binding Protein," J. Biol. Chem., vol. 269, pp. 19081–19087 (1994).

Aoki et al, "Isolation of human uteroglobin from blood filtrate," Mol. Hum. Reprod., vol. 2, pp. 489–497 (1996).

Assmann et al, "Familial Glomerulonephritis Characterized by Massive . . . ," Am. J. Kid. Dis., vol. 25, pp. 781–791 (1995).

Barnes et al, "Structural Basis for Calcium . . . ," JMB, vol. 256, pp. 392–404 (1996).

Barton et al, "Amino acid sequence analysis of the . . . ," Eur. J. Biochem., vol. 198, pp. 749–760 (1991).

Beier, H.M., "Uteroglobin: A hormone–dependent endometrial protein involved in blastocyst development," Biochim. Biophys. Acta, vol. 160, pp. 289–291 (1968).

Berenbaum, F., "Phospholipase A2 inhibitors: a challenge for the future," Ref. Rhum. Engl. Ed., vol. 62, pp. 409–414 (1995).*.

Bernard et al, "Serum Clara Cell Protein: An Indicator . . . ," Env. Res., vol. 66, pp. 96–104 (1994).

Bernard et al, "Clara cell protein in serum and bronchoalveolar lavage," Eur. Respir. J., vol. 5, pp. 1231–1238 (1992a).

Bernard et al, "Human urinary protein 1: Evidence for identity with the Clara cell protein and occurrence in respiratory tract and urogenital secretions," Clin. Chim. Act., vol. 207, pp. 239–249 (1992b).

Bernard et al, "Selective increase in the urinary excretion of protein 1 (Clara cell protein) and other low molecular weight proteins during normal pregnancy," Scand. J. Clin. Lab. Invest., vol. 52, pp. 871–878 (1992c).

Bernard et al, "Protein 1 is a Secretroy Protein for the Respiratory and Urogenital Tracts Identical to the Clara Cell Protein," Clin. Chem., vol. 38, pp. 434–435 (1992d).

Bernard et al, "Determination by latex immunoassay of protein 1 in normal and pathological urine," Clin. Chim. Acta., vol. 201 pp. 231–246 (1991).

Bernard et al, "Urine Protein 1: a Sex–Dependent Marker of Tubular or Glomerular Dysfunction," Clin. Chem., vol. 35, pp. 2141–2142 (1989).

Bitterman e t al, "Role of Fibronectin as a . . . ," J. Cell. Biol., vol. 97, pp. 1925–1932 (1983).

Camussi et al, "Anti–inflammatory peptides (antiflammins) inhibit synthesis of platelet–activating factor, neutrophil aggregation, and chemotaxis, and intradermal inflammatory reactions," J. Exp. Med., vol. 171, pp. 913–927 (1990).*.

Camussi et al., "Antiflammins Inhibit Synthesis of Platelet–Activating . . . ," Biochem, Mol. Biol., and Physiol. of Phospholipase A2 and its Regulatory Factors, pp. 161–172 (1990).

Chan et al, "Antiflammins: Inhibiton of Endotoxin–induced Uveitis in Lewis Rats," In Ocular Immunology Today (Usui, Ohno, and Aoki, Eds.), Elsevier Science Publishers, Amsterdam, pp. 467–470 (1990).

Chan et al, "Effects of Antiflammins on Endotoxin–Induced Uveitis in Rats," Arch. Opthamol., vol. 109, pp. 278–281 (1991).

Daly et al, "Bleomycin Induces Strain–Dependent . . . ," Tox. App. Pharm., vol. 142, pp. 303–310 (1997).

Dennis et al, "Multiple forms of phsopholipase A2 in macrophages capable of arachidonic acid release for cicosanoid biosynthesis," Adv. Prostaglandin Thromboxane Leukot Res., vol. 23, pp. 75–80 (1995a).*.

Dennis, E.A., "Potential phopholipase A2s involved in inflammatory diseases," Agents Actions Suppl., vol. 46, pp. 35–39 (1995b).*.

Dhanireddy et al, "Detection of a rabbit uteroglobin–like protein in human neonatal tracheobronchial washings," Biochim. Biophys. Res. Commun., vol. 152, p. 1447 (1988a).

Dhanireddy et al, "Uteroglobin–like Protein Levels in Premature Infants on Long Term Ventilator Support," Ped, Res., vol. 33, p. 323A (1993).

Dhanireddy et al, "Uteroglobin–like Protein in Premature Infants: Effect of Gestational Age," Ped. Res., vol. 23, pp. 463A (1988b).

Dhanireddy et al, "Ontogeny of Uteroglobin in Relation to . . . ," Pd. Res., 299A.*.

Dierynck et al, "Potent Inhibiton of Both Human Interferon–γ Production and . . . ," Am. J. Respir. Cell. Mol. Biol., vol. 12, pp. 205–210 (1995).

Dierynck et al, "The human Clara cell protein: biochemical and biological . . . ," Mult. Schler., vol. 1, No. 6, pp. 385–387 91996).*.

Edelson et al, "Acute Lung Injury . . . ," Am. Rev. Respir. Dis., vol. 143, pp. 1102–1109 (1991).

Facchiano et al, "Inhibition of Pancreatic Phospholipase A2 Activity by . . . ," Life Sci., vol. 48, pp. 453–464 (1990).

Fung et a l, "Coming of age for the treatment . . . ," J. Respir. Dis., vol. 13, pp. 609–619 (1992).

Gerdes et al, "Tracheal lavage and plasma . . . ," J. Pediatrics, vol. 108, pp. 601–606 (1986).

Glaser, K.B., "Regulation of phospolipase A2 enzymes: selective inhibitors . . . ," Adv. Pharmacol., vol. 32, pp. 31–66 (1995).

Groneck et al, "Association of Pulmonary Inflammation . . . ," Pediatrics, vol. 93, pp. 712–718 (1994).

Guy et al, "Surfactant–producing Rabbit Pulmonary Alvcolar Type II Cells . . . ," BBRC, vol. 189, pp. 662–669 (1992).*.

Hard et al, "Solution structure of a mammalian PCB–binding protein in complex with a PCB," Nat. Struct. Biol., vol. 2, pp. 983–989 (1995).

Ialenti et al., "Anti–inflammatory effects of vasocortin and nonapeptide fragments . . . ," Agents Actions, vol. 29, pp. 48–49 (1990).

Jackson et al, "Purification and Partial Amino Acid Sequence of Human Urine Protein 1: Evidence for . . . ," J. Chromatog., vol. 452, pp. 359–367 (1988).

Krishnan et al, "'Blastokinin': Inducer and Regulator of Blastocyst . . . ," Science, vol. 158, pp. 490–492 (1967).

Kundu et al, "Recombinant human uteroglobin suppresses cellular . . . ," PNAS, vol. 93, pp. 2915–2919 (1996).

Lesur et al, "Clara Cell Protein (CC–16) Induces a Phospholipase . . . ," Am. J. Respir. Crit. Care Med., vol. 152, pp. 290–297 (1995).

Lesur et al, "Clara–Cell Protein (CC–16) and Surfactant . . . ," Chest, vol. 109, pp. 467–474 (1996).

Levin et al, "Uteroglobin inhibits phospholipase A2 activity," Life Sci., vol. 38, pp. 1813–1819 (1986).

Leyton et al, "Recombinant Human Uteroglobin Inhibits the in Vitro Invasiveness . . . ," Can. Res., vol. 54, pp. 3696–3699 (1994).

Lloret et al, "Effect of nonapeptide fragments . . . ," Eur. J. Pharm., vol. 264, pp. 379–384 (1994).

Manjunath et al, "Crosslinking of Uteroglobin by Transglutaminase," BBRC, vol. 121, pp. 400–407 (1984).

Manjunath et al, "Inhibition of Thrombin–induced Platelet Aggregation by Uteroglobin," Biochem. Pharmacol, vol. 36, pp. 741–746 (1987).

Mantile et al, "Human clara cell 10 kDa protein is the counterpart of rabbit uteroglobin," J. Biol. Chem., vol. 268, pp. 20343–20351 (1993).

Miele et al, "Uteroglobin and uteroglobin–like proteins. The uteroglobin family of proteins," J. Endocrinol. Invest., vol. 8, pp. 679–692 (1994).

Miele et al, "High Level Bacterial Expression of Uteroglobin, a Dimeric . . . ," J. Biol. Chem., vol. 265, pp. 6427–6435 (1990).

Miele et al, "Uteroglobin: structure, molecular biology, and new perspectives on its function as a phospholipase A2 inhibitor," Endocr. Rev., vol. 8, pp.e 474–490 (1987).

Miele et al, "Novel anti–inflammatory peptides from the region of highest similarity between . . . ," Nature, vol. 335, pp. 726–730 (1988).

Mihal, K., "One gene encoding three proteins with different functions," Am. J. Respir. Cell. Mol. Biol., vol. 5, pp. 1–3 (1991).

Mukherjee et al, "Phospholipase A2 Enzymes . . . ," Biochem. Pharmacol., vol. 48, pp. 1–10 (1994).

Mukherjee et al, "Regulation of Extracellular Phospholipase A2 Activity: Implications for . . . ," DNA and Cell Biology, vol. 11, pp. 233–243 (1992).

Mukherjee et al, "Modulation of cellular response to antigens by uteroglobin and transglutaminase," In: Adv. Post–Trans Modif Proteins & Aging, (Zappia, V., Galletti, P. Eds.), New York, NY, Plenum Press, pp. 135–152 (1988).

Nomori et al, "Protein 1 (Clara Cell Protein) Serum Levels in Healthy . . . ," Am. J. Respir, Crit. Care Med., vol. 152, pp. 746–750 (1995).

Nomori et al, "Protein 1 and Clara cell 10–kDa protein distribution in normal and neoplastic tissues with emphasis on the respiratory system," Virchows Archiv., vol. 424, pp. 517–523 (1994).

Nord et al, "Calcium–dependent binding of uteroglobin (PCB–BP/CCSP) to . . . ," FEBS Lett., vol. 374, pp. 403–306 (1995).

Okutani et al, "Simple and high–yield purification of urine protein 1 using . . . ," J. Chromatog, vol. 577, pp. 23–35 (1992).

Peri et al, "Uteroglobin gene expression in the rabbit uterus throughout gestation and in the fetal lung: Relationship between . . . ," J. Clin. Invest., vol. 96, pp. 343–353 (1995).

Peri et al, "Tissue–specific expression of the gene coding for human cc 10kDa . . . ," J. Clin. Invest., vol. 92, pp. 2099–2109 (1993).

Peter et al, "Recombinant uteroglobin expressed at high levels . . . ," Prot. Eng., vol. 3, pp. 61–66 (1989).

Peteres et al, "Clinical determinants of abnormalities in pulmonary functions in survivors of . . . ," Am. Rev. Respir. Dis., vol. 139, pp. 1163–1168 (1989).*.

Piomelli et al, "Arachidonic acid in cell signaling," Curr. Op. in Cell. Biol., vol. 5, pp. 274–280 (1993).

Ray et al, "Cloning and Characterization of the Mouse Clara Cell Specific 10 kDa Protein Gene: Comparison of the . . . ," BBRC, vol. 197, pp. 163–171 (1993).

Robinson et al, "Macromolecular transport in rabbit . . . ," Mol. Cell Endocrin., vol. 63, pp. 227–237 (1989).

Ruoslahti et al, "Fibronectin and Its Receptors," Ann. Rev. Biochem., vol. 57, pp. 374–413 (1988).

Scheuer, W., "Phospholipase A2–regulation and inhibition," Klin Wochenschr, vol. 67, pp. 153–159 (1989).

Shijubo et al, "Serum and BAL Clara cell 10 kDa protein (CC10) levels and CC10–positive bronchiolar cells are decreased in smokers," Eur. Respir. J., vol. 10, pp. 1108–1114 (1997).

Singh et al, "Isolation and Amino Acid Composition . . . ," Exp. Lung Res., vol. 13, pp. 299–309 (1987).

Singh et al, "Identification, Cellular Localization, Isolation, and Characterization of Human Clara Cell–Specific 10 KD Protein," J. Hist. Cyt., vol. 36, pp. 73–80 (1988b).

Singh et al, "Clara cell 10 kDa protein (CC10): comparison . . . ," Biochim. Biophys. Acta., vol. 1039, pp. 348–355 (1990).

Singh et al., "Mouse Clara Cell 10 kDa protein (CC10) Protein: cDNA . . . ," Exp. Lung Res., vol. 19, pp. 67–75 (1993).

Stenmark et al, "Potential role of cicosanoids and platelet–activating factor in the pathophysiology of BPD," Am. Rev. Resp. Dis., vol. 136, pp. 770–772 (1987).

Stripp et al, "cis–Acting Elements that Confer Lung . . . ," JBC, vol. 267, pp. 14703–14712 (1992).

Stripp et al, "Structure and Regulation of the Murine Clara . . . ," Genomics, vol. 20, pp. 27–35 (1994).

Stripp et al, "Plasticity of airway cell proliferation and gene expression after acute naphthalene injury," Am. J. Physiol., vol. 269, pp. L791–L799 (1995).

Stripp et al, "Clara cell secretory protein: a determinant of PCB bioaccumulation in mammals," Am. J. Physiol., 271 (Lung Cell Mol. Physiol. 15), pp. L656–L664 (1996).

Umland et al, "Structure of human Clara cell phopholipid–binding protein–ligand complex at 1.9 A resolution," Nature Struct. Biol., vol. 1, pp. 538–545 (1994).

Umland et al, "Twixt form and function," Nat. Struct. Biol., vol. 2, pp. 919–922 (1995).

Vadas et al, "Potential therapeutic efficacy of inhibitors of . . . ," Agents Actions, vol. 19, pp. 194–202 (1986).*.

Van Bisbergen et al, "Synthetic peptide from lipocortin 1 has no phospholipase inhibitory activity," FEBS Lett., vol. 247, pp. 293–297 (1989).

Van Winkle et al, "Repair of Naphthalene–injured Microdissected . . . ," Am. J. Respir. Cell. Mol. Biol., vol. 15, pp. 1–8 (1996).

Vasanthakumar et al, "Inhibition of phagocyte chemotaxis by potent phospholipase A2 inhibitory protein, Uteroglobin," Biochem. Pharm., vol. 37, pp. 389–394 (1988).

Volovitz et al, "Relationship between Leukotriene C4 and an Uteroglobin–like Protein . . . ," Int. Arch. Allergy Appl. Immunol., vol. 86, pp. 420–425 (1988).

Vostal et al, "Novel peptides derived from a region of local . . . ," BBRC, vol. 165, pp. 27–36 (1989).

Wu et al, "Integrin Activation and Cytoskeletal Interaction . . . ," Cell, vol. 83, pp. 715–724 (1995).

Wuenschell et al, "Embryonic mouse lung epithelial progenitor cells . . . ," J. Histochem Cytochem, vol. 44, pp. 113–123 (1996).

Zhang et al, "Cross–linking of the NH2–terminal Region of Fibronectin . . . ," JBC, vol. 271, pp. 33284–33292 (1996).

Zhang et al, "Modulation of Cell Surface Fibronectin Asembly Sites by Lysophosphatidic Acid," J. Cell Biol., vol. 127, pp. 1447–1459 (1994).

Zhang et al., "Human Uteroglobin Gene: Structure . . . ," DNA & Cell Biology, vol. 16, pp. 73–83 (1997).

Camussi et al, "Anti–inflammatory peptides (antiflammins) inhibit synthesis of platelet–activating factor, neutrophil aggregation, and chemotaxis, and intradermal inflammatory reactions," J. Exp. Med., vol. 171, pp. 913–927 (1990).

Dennis et al, "Multiple forms of phospholipase A2 in macrophages capable of arachidonic acid release for cicosanoid biosynthesis," Adv. Prostaglandin Thromboxane Leukot Res., vol. 23, pp. 75–80 (1995a).

Dennis, E.A., "Potenial phopholipase A2s involved in inflammatory diseases," Agents Actions Suppl., vol. 46, pp. 35–39 (1995b).

Dhanireddy et al, "Ontogeny of Uteroglobin in Relation to . . . ," Pd. Res., 299A.*.

Dierynck et al, "The human Clara cell protein: biochemical and biological . . . ," Mult. Schler., vol. 1, No. 6, pp. 385–387 91996).

Guy et al, "Surfactant–producing Rabbit Pulmonary Alvcolar Type II Cells . . . ," BBRC, vol. 189, pp. 662–669 (1992).

Vadas et al, "Potential therapeutic efficacy of inhibitors of . . . ," Agents Actions, vol. 19, pp. 194–202 (1986).*.

Tykka et al. A randomized double–blind study using CaNa2EDTA, a phospholipase A2 inhibitor, in the management of human acute pancreatitis. Scan. J. Gastroenterology, (Jan. 1985) 20 (1) 5–12.*

Tykka et al. Phospholipase A2 inhibitors and their possible clinical use in the treatment of acute pancreatitis. Scand J Gastroenterol 1980;15(5):519–28, Abstract only.*

Olson et al. Know your neighbors: three phenotypes in null mutants of the myogenic bHLH gene MRF4. Cell Apr. 1996 5;85(1):1–4.*

* cited by examiner

HUMAN CC10 kDa: 1 EICPSFQRVIETLLMDTPSSYEAAMELFSPDQDMREAGAQLKKLVDTLPQKPRESIIKLMEKIAQSSLCN 69

RABBIT Utg:     ICP F  VIE LL  TPSSYE      F PD  M  AG Q KK   D LPQ  RE  I  KL EKI    S LC
                GICPRFAHVIENLLLGTPSSYETSLKEFEPDDTMKDAGMQMKKVLDSLPQTTRENIMKLTEKIVKSPLC

RAT CC10:       ICP F  V E LL     S YEAA    F P  D    AG QLK  LVDTLPQ   R   I  KL  EKI    S LC
                DICPGFLQVLEALLGSESNYEAALKPFNPASDLQNAGTQLKRLVDTLPQETRINIVKLTEKILTSPLCEQDLRV

MOUSE CC10:     ICP F  V E LLM    S Y A     F P  D    AG QLK  LVDTLPQ   R   I  KL  EKI    S LC
                DICPGFLQVLEALLMESESGYVASLKPFNPGSDLQNAGTQLKRLVDTLPQETRINIMKLTEKILTSPLCKQDLRF

ALIGNMENT OF UG-LIKE PROTEINS, INCLUDING HUMAN CC10, RABBIT UTEROGLOBIN, RAT AND MOUSE CC10. FOR COMPARISON, AMINO ACID RESIDUES ARE SHOWN ABOVE THE PRIMARY SEQUENCES CORRESPOND TO RESIDUES FOUND AT THE SAME POSITION IN THE HUMAN PROTEIN. THESE SEQUENCES ARE PREDICTED BY TRANSACTION OF THE NUCLEOTIDE SEQUENCES DEPOSITED IN THE GENEBANK. THESE PROTEINS ARE SECRETED PROTEINS AND THE N-TERMINAL SIGNAL SEQUENCES, THAT ARE TRANSLATED AND PROCESSED OFF, HAVE BEEN EDITED OUT FOR THIS COMPARISON.

FIG. 1

FIG. 2A
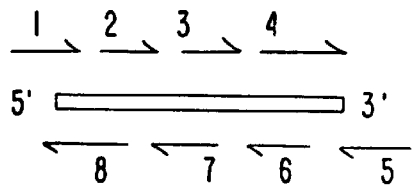
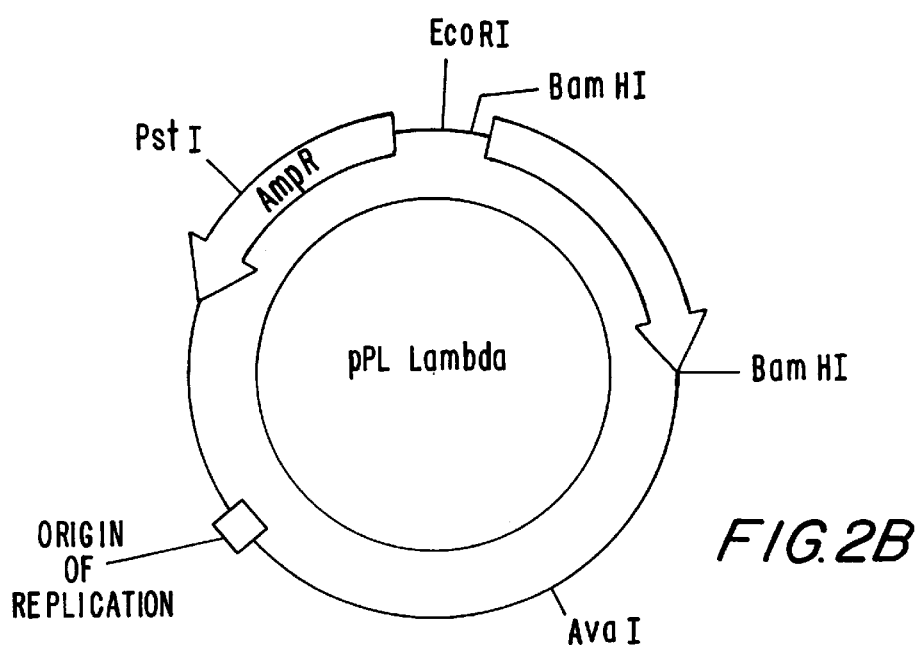
FIG. 2B
AMPLIFY FROM TEMPLATE
FIG. 2C    CUT WITH RESTRICTION ENZYMES
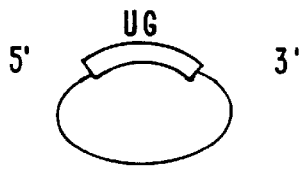
LIGATE INTO LINEARIZED EXPRESSION VECTOR

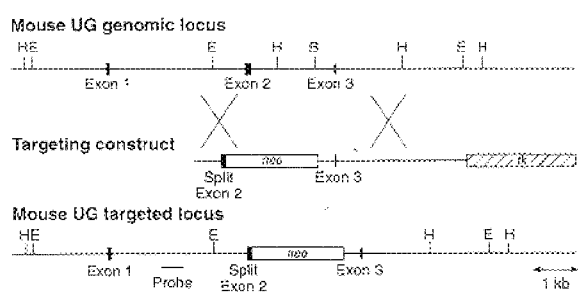
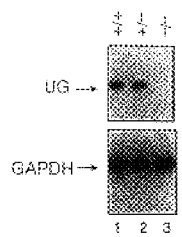
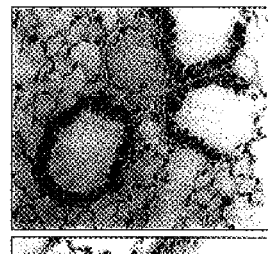
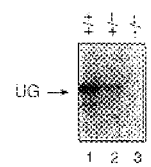
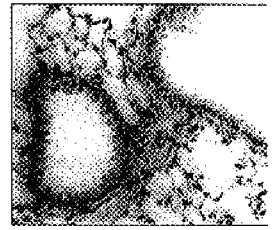
FIG. 3A
FIG. 3E
FIG. 3B  FIG. 3C  FIG. 3D
FIG. 3F
FIG. 3G

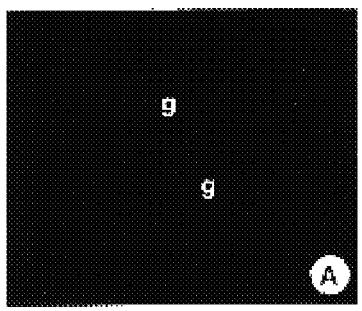
FIG. 6A
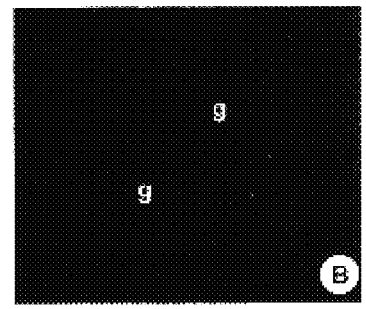
FIG. 6B
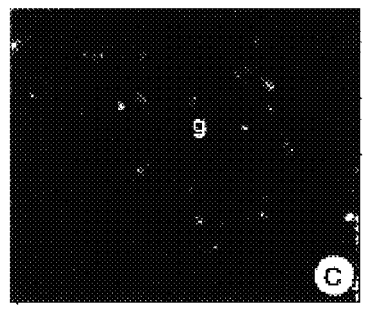
FIG. 6C
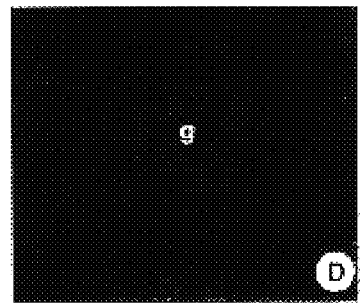
FIG. 6D
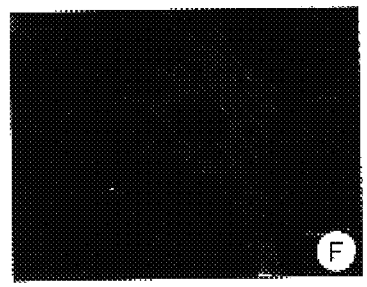
FIG. 6F
FIG. 6E

USE OF RECOMBINANT HUMAN UTEROGLOBIN IN TREATMENT OF INFLAMMATORY AND FIBROTIC CONDITIONS

FIELD OF THE INVENTION

The present invention relates generally to the treatment of inflammatory and fibrotic conditions. More particularly, the invention provides a method for the treatment of inflammatory and fibrotic disease using recombinant human uteroglobin (rhUG). The invention identifies novel physiological roles for UG and their applications. Even more specifically, the invention relates to the treatment of inflammatory and fibrotic conditions by administering rhUG to inhibit $PLA_2$s in vivo and to prevent fibronectin deposition in vivo. The invention further provides a method for the treatment of neonatal RDS/BPD, a critical clinical condition of the lung, and glomerular nephropathy, a disease of the kidney, both characterized by the involvement of inflammatory and fibrotic components.

BACKGROUND OF THE INVENTION

The search for improved therapeutic agents for the treatment of inflammatory, as well as fibrotic diseases, has received much attention in recent years. Neonatal Respiratory Distress Syndrome (RDS), a lung surfactant deficiency disease, is a condition of particular interest in that it is one of the major causes of mortality in premature neonates. While introduction of surfactant therapy dramatically improves survival of RDS patients, the development of chronic inflammatory and fibrotic disease in a significant percentage of this patient population is a major problem. Likewise, hereditary fibronectin-deposit glomerular nephropathy leads to end stage renal failure when patients' kidneys become blocked and no longer filter the blood. Hereditary glomerular nephropathy is characterized by fibronectin deposits and fibrosis of the kidneys. In both diseases, fibronectin deposition and fibrosis render the organ non-functional, and eventually, unable to support life. Thus, these patients require chronic hemodialysis or kidney transplantation.

$PLA_2$ is one of the enzymes responsible for hydrolysis of the surfactant phospholipids. Human uteroglobin, also known as "CC10", inhibits the activity of phospholipase $A_2$ ($PLA_2$) in vitro [Levin, S. W., et al. Uteroglobin inhibits phospholipase $A_2$ activity. Life Sci. 38:1813–1819 (1986); Singh, G. et al. Clara Cell 10 kda protein (CC10): Comparison of Structure and Function to Uteroglobin. Biochem. Biophys. Acta. 1039:348–355 (1990); Mantile, G. et al Human Clara Cell 10 kDa Protein Is The Counterpart of Rabbit Uteroglobin. J. Biol. Chem. 268:20343–20351 (1993)]. Human uteroglobin was first isolated in 1988 as a secretion product from the Clara cells of the lungs (Singh, G., et al. Identification, Cellular Localization, Isolation and Characterization of Human Clara Cell-Specific 10 kD Protein. J. Histochem. Cytochem., 36:73–80 (1987). (The designation "CC10" was derived from "Clara cell 10 kDa".). It is a small globular homodimeric protein, and migrates in electrophoretic gels at a size corresponding to 10 kDa (Singh, G., et al. Identification, Cellular Localization, Isolation and Characterization of Human Clara Cell-Specific 10 kD Protein. J. Histochem.Cytochem., 36:73–80 (1987). (The designation "CC10" was derived from "Clara cell 10 kDa"). Human uteroglobin (hUG) is abundant in the adult human lung, and comprises up to about 7% of the total soluble protein (Bernard, A. et al, Protein 1 is a Secretory Protein of the Respiratory and Urogenital tracts identical to the Clara Cell Proteins. Clin. Chem. 38:434–435 (1992)). However, its expression is not fully activated in developing human fetus until the last few weeks of gestation. Consequently, the extracellular lung fluids of pre-term infants contain less human UG than those of adults, and may be deficient in these neonates (Dhanireddy, R., El-Ali, M., Murty, L., and A. B. Mukheijee, Pediatric Research 23:463A (1988) and Dhanireddy, R., Lim, M., and A. B. Mukheijee, Pediatric Research 33:323A (1993)).

$PLA_2$s are a class of endogenous enzymes that hydrolyze the sn2 position ester bond of glycerophospholipids. They play critical roles in the inflammatory response because they release arachidonic acid (AA) from cellular phospholipid reservoirs. AA is metabolized to a number of potent inflammatory mediators in a process referred to as the arachidonic acid cascade (Piomelli, D. Arachidonic Acid in Cell Signaling. Op. In Cell Biol. 5:274–280 (1993)). Several acute and chronic clinical conditions have been characterized with elevated serum or local $PLA_2$ activity (see Table below). Native rabbit uteroglobin (UG), discovered in 1967 and purified from uteri of pregnant rabbits (Krishnan, R. S. and Daniel, J. C., Jr. "Blastokinin: Inducer and Regulator of Blastocyst Development in the Rabbit Uterus." Science 158:490–492 (1967); Beier H. M. Verhandl Deut. Zool. Ges., Heidelberg (1968)), inhibits $PLA_2$ activity in vitro (Levin, 1988; supra). Clinical conditions in which elevated $PLA_2$ activity is documented are set forth in the following Table.

TABLE

| Diseases | Sites |
|---|---|
| Rheumatoid arthritis | Serum, synovial fluid, WBC |
| Collagen vascular diseases | Serum |
| Pancreatitis | Serum |
| Peritonitis | Peritoneal fluid and cells |
| Septic shock | Serum |
| ARDS[a] | Serum and alveolar fluid |
| Acute renal failure | Serum |
| Autoimmune uveitis | Serum, aqueous humor |
| Bronchial asthma | Bronchial fluid |

[a]Adult respiratory distress syndrome
(Modified from Mukherjee et al, 1992)

Amino acid analysis of purified human UG reveals that it is structurally similar to rabbit UG but not identical. 37 of 70 amino acids are identical between human and rabbit UG (see FIG. 1). The "UG-like" proteins, including human UG/CC10, rat CC10, mouse CC10 and rabbit UG, exhibit species-specific and tissue-specific antigenic differences, as well as differences in their tissue distribution and biochemical activities in vitro. UG-like proteins have been described in many different contexts with regard to tissue and species of origin, and have also been identified using numerous different names, including uteroglobin, blastokinin, CC10 kDa protein (from rat lung), urine-protein 1 or "P1" (human), progesterone-binding protein (rabbit uterus), PCB-binding protein (rat lung), and CC16 (human lung), which has created confusion in the literature. At present there are no known physiological roles for these proteins (Umland, T. C., et al. Structure of a Human Clara Cell phospholipid-binding protein-ligand, complex at 1.9 Aresolution, Nature Struct. Biol. 1:538–545 (1994); Hard, T. et al, Solution Structure of Mammalian PCB-binding Protein in Complex with a PCB. Nat. Struct. Biol. 2:983–989 (1995); Umland, T. C. and M. Sax. Twixt form and function. Nat. Struct. Biol. 2:919–922 (1995); Stripp, B. R., et al. Clara cell secretory protein: a determinant of PCB bioaccumulation in mammals. Am. J. Physiol. 271 (Lung Cell. Mol. Physiol. 15): L656–L664 (1996).

The absence of structural identity among UG-like proteins makes it impossible to predict whether a protein will possess in vivo function based on in vitro or other activity exhibited by a structurally related protein in the context of an human therapeutic. For example, human uteroglobin binds less than 5% of the amount of progesterone than rabbit UG binds in the same assay (Singh, G., et al. Clara Cell 10 kDa Protein (CC10): Comparison of Structure and Function to Uteroglobin. Biochem Biophys Acta 1039:348–355 (1990). Human UG has a lower isoelectric point (4.6) than rabbit UG (5.4). Moreover, a UG knockout mouse recently generated to eliminate expression of UG has Clara cells which exhibit odd intracellular structures in place of UG secretion granules, but there is no other phenotype. This observation is highly significant since the anticipated phenotype was inefficient pulmonary finction accompanied by pulmonary inflammation and fibrosis. The knockout mouse shows no evidence of pulmonary impairment or abnormality, indicating that the UG protein has no significant role in surfactant homeostasis as had been previously suggested (Lesur, O., et al. Clara Cell Protein (CC16) Induces a Phospholipase $A_2$-mediated Inhibition of Fibroblast Migration in Vitro. Am. J. Respir. Crit. Care Med. 152:290–297 (1995); Umland, T. C., et al, 1994; supra).

Despite years of studies and accumulation of data on UG-like proteins, the biological roles of these proteins and their inhibitory effect in vivo on $PLA_2$s and the inflammatory process remains unclear. There are no effective $PLA_2$ inhibitors presently available for clinical use. To date, only a few $PLA_2$ inhibitors have progressed into clinical trials, but none have qualified for commercial marketing.

Fibronectin (Fn) is a 200 kDa glycoprotein which exists in several different forms and is secreted by different tissues. Fn is an essential protein and attempts to generate knockout mice showed that it has a central role in embryogenesis. Fn also plays a key role in inflammation, cell adhesion, tissue repair and fibrosis, and is deposited at the site of injury. Plasma fibronectin, (pFn) is secreted by the liver and circulates in the plasma. In the lung, cellular Fn (cFn) is secreted upon inflammation and injury. Both types of Fn are chemotactic factors for inflammatory cells and fibroblasts. Large numbers of inflammatory cells (neutrophils) and fibroblasts infiltrate the lung during inflammatory episodes, which can lead to pulmonary fibrosis and ultimately death. Elevated levels of Fn have been detected in human clinical conditions such as neonatal RDS and BPD of the lung, and glomerular nephropathy of the kidney.

An urgent need exists for an effective agent for treating inflammatory conditions, particularly RDS, and fibrotic diseases where fibronectin deposition is a causative factor, which does not cause deleterious side-effects. The present invention discloses novel physiological functions of UG and seeks to fill that need.

SUMMARY OF THE INVENTION

The present invention is directed to the surprising discoveries that UG plays a central physiological role in prevention of fibronectin deposition and fibrosis and in vivo inhibition of $PLA_2$s through a combination of experiments done in a new strain of transgenic UG "knockout" mice, and in a monkey model of neonatal respiratory distress syndrome (RDS) which involves pulmonary inflammation and fibrosis. The UG knockout mice exhibit lethal glomerular nephropathy and renal parenchymal fibrosis, as early and late onset diseases, respectively. Administration of recombinant human UG (rhUG) to the UG knockout mice inhibits Fn deposition in the kidneys.

Furthermore, the actual reduction of $PLA_2$ activity in vivo is demonstrated in the presence of UG with two experiments: 1) the phenotype of the UG knockout mice further reveals that serum $PLA_2$ activity is significantly elevated in the absence of UG, compared to littermates possessing a functional UG gene; and 2) administration of rhUG to pre-term monkeys suffering from RDS inhibits $PLA_2$ activity, in the extracellular fluids of the lungs. In vitro $PLA_2$ can degrade the artificial surfactant (typically Survanta) used in treatment of RDS and rhUG can inhibit this degradation. Moreover, UG-Fn complexes can be detected in samples through the use of a new solution phase sandwich assay for the complex. The results of these experiments demonstrate that rhUG does, in fact, mediate $PLA_2$ inhibition and Fn deposition in vivo following intratracheal or intravenous administration.

The UG knockout mouse of the present invention further demonstrates that rhUG may be used to treat conditions in which UG is found to be deficient, or the protein itself bears a loss-of-function mutation. In particular, according to the present invention, rhUG may be used to treat or prevent inflammatory or fibrotic conditions in which functional endogenous UG is deficient in the circulation or at the site of inflammation or fibrosis. Normal ranges for UG in bodily fluids have been primarily characterized (Bernard, A., et al. Human Urinary Protein 1: Evidence for Identity with the Clara cell protein and occurrence in respiratory tract and urogenital secretions. Clin. Chim. Acta 207: 239–249 (1992)). Reductions in the levels of UG in serum and/or broncho-alveolar lavage fluids have been found in certain pulmonary inflammatory or fibrotic conditions (Lesur, O., et al. Clara Cell Protein (CC-16) Induces a Phospholipase $A_2$-mediated Inhibition of Fibroblast Migration In Vivo. Am. J. Respir. Crit. Care Med. 152: 290–297 (1995)), including pre-term infants at risk for developing neonatal BPD (Dhanireddy, R., et al. Uteroglobin-like protein in premature infants: Effect of gestational age. Pediatric Research 23: 463A (1988)). The present invention provides an understanding of the mechanisms through which therapeutic intervention through UG replacement can be achieved. Therefore, rhUG may be used to supplement deficient or defective endogenous UG to prevent or treat such inflammatory and fibrotic conditions.

According to one aspect, the present invention provides a method of treating an inflammatory condition in vivo comprising administering to a patient in need of such treatment an anti-inflammatory effective amount of rhUG.

According to a further aspect, the present invention provides a method of inhibiting $PLA_2$ enzymes in vivo, which comprises administering to a patient in need of such treatment an $PLA_2$ inhibiting effective amount of rhUG.

In accordance with yet a furfther aspect, the present invention provides a method for treating or preventing a fibrotic condition, which comprises administering to a patient in need of such treatment a fibronectin binding effective amount of rhUG.

In accordance with a further aspect, the present invention provides a method for treating or preventing an inflammatory or fibrotic condition characterized by a deficiency of endogenous functional UG, which comprises administering to a patient in need of such treatment a compensating amount of rhUG.

The invention also provides pharmaceutical compositions comprising an effective amount of rhUG in association with a pharmaceutically acceptable carrier or diluent. The compositions may take the form of injectable solutions and semi-aerosols (intratracheal administration).

According to a further aspect, the invention provides pharmaceutical compositions comprising rhUG and a lung surfactant, in association with a pharmaceutically acceptable carrier or diluent. Examples of typical lung surfactants are Survanta (a bovine lung extract from Abbott Labs) and Exosurf (a chemically synthetic lung surfactant from Glaxo-Wellcome).

In another aspect, the invention provides an assay for quantitating uteroglobin-fibronectin complexes in a clinical sample, wherein a clinical sample suspected of containing uteroglobin-fibronectin complex is contacted with an antigen capture agent, for example a monospecific rabbit polyclonal antibody, immobilized on an insoluble support. An antigen detection agent, for example an antibody specific for fibronectin, is added to the sample. The presence of any said complex bound to said support is detected using, for example, anti-IgG antibody conjugated to an enzyme such as horse radish peroxidase using a standard enzymatic reaction wherein the enzyme substrate is converted to a chromogenic or fluorogenic compound which is quantitated using standard spectrophotometric or fluorometric apparatus.

The anti-inflammatory and anti-fibrotic effects in vivo obtained according to the present invention are surprising and unpredictable. There was no evidence prior to the present invention that $PLA_2$ inhibitors could reduce or prevent inflammatory disease in vivo (Glaser KB. Regulation of phospholipase $A_2$ enzymes: selective inhibitors and their pharmacological potential. Adv Pharmacol. 32: 31–66 (1995)). For example, a $PLA_2$ inhibitor, CaNa2-EDTA, did not significantly affect the clinical outcome in pancreatitis, a condition characterized by elevated serum $PLA_2$ activity (Tykka, H. T., et al. A Randomized Double-Blind Study Using CaNa2EDTA, a Phospholipase $A_2$ Inhibitor, in the Management of Human Acute Pancreatitis. Scand. J. Gastroenterol. 20:5–12 (1985)). Moreover, as noted above, a recently constructed putative UG knockout mouse model appears to be normal, exhibiting no signs of inflammatory disease (Stripp, 1996, supra). In addition, $PLA_2$ enzymes affect many physiological processes and, despite extensive study of many $PLA_2$ inhibitors, none is used in any clinical application (Sheuer, W., Phospholipase $A_2$-Regulation and Inhibition. Klin. Wochenschr. 67:153–159 (1989)). In addition, rhUG binds to phospholipids in vitro, which precludes its use in conjunction with exogenously administered surfactant for RDS (Umland, 1994; supra).

There is no information on potential toxicity to humans if a bolus of rhUG is administered into the body. It has been observed that UG binds calcium (Barnes HJ, et al. Structural basis for calcium binding by uteroglobins. J. Mol. Biol. (Feb. 23, 1996)), suggesting that introduction of a bolus of rhUG may cause a systemic imbalance of calcium. Human UG is a growth factor for some types of cells and tumors which mitigates against the use of UG (Aoki, A., et al. Isolation of human uteroglobin from blood filtrate. Mol. Hum. Reprod. 2:489–497 (1996).

Prior to the present invention, there could be no expectation that administration of rhUG in vivo would result in inhibition of $PLA_2$ enzymes or in reduced deposition of fibronectin. The present invention therefore constitutes a significant step forward in the therapy of inflammatory and fibrotic diseases.

BRIEF DESCRIPTION OF THE DRAWINGS

The invention will now be described in more detail, with reference to the accompanying drawings, in which:

FIG. 1 shows an alignment of UG-like proteins; (Human CC10 (SEQ ID NO: 1), Rabbit UG (SEQ ID NO: 2), Rat CC10 (SEQ ID NO: 3), and Mouse CC10 (SEQ ID NO: 4).

FIGS. 2A, 2B and 2C show the construction of a new gene for rhUG and its cloning into expression vector pPL-lambda;

FIG. 3A shows the intended targeting construct of the transgenic UG knockout mouse as a schematic diagram of the UG gene locus (upper panel), wherein the restriction sites are Bam HI (B), EcoRI (E), and HindIII (H);

FIGS. 3B–3D show verification of the genetic construct in progeny of transgenic embryos by PCR and Southern blot analyses; FIG. 3B shows a Southern blot analyses of the targeted ES R1 cell clones, wherein Wt=wild type; FIG. 3C shows a representative PCR analyses of genomic DNA from tail biopsies of offspring, wherein the genotypes and their corresponding PCR products are as follows: $UG^{+/+}$, 304 bp; $UG^{+/-}$, 304 and 667 bp; $UG^{-/-}$, 667 bp; and FIG. 3D shows a Southern blot of mouse tail genomic DNA;

FIG. 3E shows confirmation of the absence of UG-mRNA in the lung tissues of $UG^{-/-}$ mice by RT-PCR analysis as a RT-PCR analyses of total RNA extracted from the lung tissues of littermates with $UG^{+/+}$, $UG^{-/+}$, and $UG^{-/-}$ genotypes; a 273 bp RT-PCR product was detectable in the lungs of $UG^{+/+}$ and $UG^{+/-}$ mice but lacking from those of $UG^{-/-}$ mice;

FIG. 3F shows confirmation of the absence of UG protein in the lungs of $UG^{-/-}$ mice by Western analysis proteins (30 μg each) from lung lysates were resolved by electrophoresis using 4–20% gradient SDS-polyacrylamide gels under non-reducing conditions and immunoblotted using rabbit anti-mouse UG;

FIG. 3G shows confirmation of the absence of UG in lung tissue sections of the $UG^{-/-}$ mice using immunohistochemical methods including immunohistochemical localization of UG in bronchiolar epithelial cells, wherein the dark staining over the bronchiolar epithelial cells of a $UG^{+/+}$ mouse (upper panel) indicates UG immunoreactivity (note the absence of immunoreactivity in $UG^{-/-}$ mouse lungs (lower panel));

In FIG. 4C, kidney sections of a 10 month old mouse with severe parenchymal fibrosis are shown. In FIG. 4D a region of the same mouse kidney is shown, exhibiting renal tubular hyperplasia (magnification 40x, g=glomerulus, ƒ=fibrosis, and t=tubule). FIG. 4E shows transmission electron microscopy of the glomerular deposit of a $UG^{-/-}$ mouse with sever renal disease (magnification 6000x). FIG. 4F shows the inset in (E) magnified 60,000x, which shows the long striated fibrillar structures indicative of collagen (col) and short diffuse ones consistent with Fn fibrils. FIG. 4G shows Fn-immunofluorescence of a kidney section from a $UG^{+/+}$ mouse using murine Fn-antibody. FIG. 4H shows Fn-immunofluorescence of a kidney section from a $UG^{-/-}$ mouse with severe renal disease. Mason's trichrome staining of the kidney sections from $UG^{+/+}$ (D) and $UG^{-/-}$ (J) mice. The bluish staining over the glomeruli of $UG^{-/-}$ mouse kidney section is collagen (magnification approximately 40x).

FIGS. 6A–6F show the immunohistochemical analysis of Fn deposition in the kidneys of normal and UG$^{-/-}$ mice only in the absence of UG FIG. 6A shows kidney section of wild-type mouse that received a mixture of equimolar concentrations of Fn and UG intravenously; FIG. 6B shows a kidney section of a UG$^{+/+}$ mouse that received the same dose of Fn as in (A) but without UG; FIG. 6C shows kidney section of an apparently healthy UG$^{-/-}$ mouse receiving a mixture of Fn and UG; FIG. 6D shows a kidney section of a UG$^{-/-}$ mouse receiving Fn alone (same dose as in C), but without UG; FIG. 6E shows Fn-fibrillogenesis by cultured cells (29) grown in medium supplemented with soluble hFn alone; FIG. 6F shows a cell culture identical to that in E which was fed with medium containing a mixture of equimolar concentrations of soluble hFn and UG (magnification 40×, g=glomerulus)

FIG. 3 Targeting of the UG Locus. A. Schematic diagram of the UG gene locus (upper panel). The restriction sites are: E=BamEI, E=EcoRI, H=HindIII. B. Southen blot analyses of the targeted ES R1 cell clones. Wt=wild type. C. Representative PCR analyses of senomic DNA from tail biopsies of offspring. The genotypes and their corresponding PCR products are as follows: UG$^{+/+}$, 304 bp; UG$^{+/-}$ 304 and 667 bp; UG$^{-/-}$, 667 bp. D. Southern blot of mouse tail genomic DNA; E. RT-PCR analyses of total RNA extracted from the lung tissues of littermates with UG$^{+/+}$, UG$^{+/-}$ and UG$^{-/-}$ genotypes. A 273 bp RT-PCR product was detectable in the lungs of UG$^{+/+}$ and UG$^{+/-}$ mice but lacking from those of UG$^{-/-}$ mice. F. Western blot analysis. Proteins (30 μg each) from luna lysates were resolved by eflctrophoresis using 4–20% gradient SDS-polyacrylamide gels under non-reducing conditions and iumnunoblotted using rabbit anti-mouse UG. G. Immunohistochemical localization of UG in bronchiolar epithelial cells. The dark staining over the bronchiolar epithelial cells of a UG$^{+/+}$ mouse (upper panel) indicates UG immunoreactivity. Note the absence of immunoreactivity in UG$^{-/-}$ mouse lungs (lower panel). Methods are described in (17–19, 31).

FIG. 4 Severe Renal Glomerular Disease in UG$^{-/-}$ Mice. H & E staining of kidney sections from a UG$^{+/+}$ (A) and its UG$^{-/-}$ (B) littermate. C. Kidney section of a 10 month old mouse with severe parenchymal fibrosis. D. A region of the same mouse kidney in (C), showing renal tubular hyperplasia. Magnification 40×. g=glomerulus; f=fibrosis; t=tubule. E. Transmission Electron Microscopy of the glomerular deposit of a UG$^{-/-}$ mouse with severe renal disease. Magnification 6000×. F. The inset in (E) is magnified 60,000×, which shows the long striated fibrillar structures indicative of collagen (col) and short diffuse ones consistent with Fn fibrils. G. Fn-immunofluorescence of a kidney section from a UG$^{+/+}$ mouse using murine Fn-antibody. H. Fn-immunofluorescence of a kidney section from a UG$^{-/-}$ mouse with severe renal disease. Mason's trichrome staining of the kidney sections from UG$^{+/+}$ (I) and UG$^{-/-}$ (J) mice. The bluish staining over the glomeruli of UG$^{-/-}$ mouse kidney section is collagen. Magnification, approximately 40×.

FIG. 5. Detection or Multimeric Fn in UG$^{-/-}$ Mice and the Effect of UG on Fa-Fn and Fn-Collagen Interactions. (A) Immrunoprecipition (18) and Western blotting of Fn from plasma, kidney and liver of UG$^{+/+}$ and UG$^{-/-}$ mice. A multimeric Fn band (bold arrow) was detected only in the kidney lysates of UG$^{-/-}$ mice. (B) Equimolar concentrations of UG and Fn were incubated, immnunoprecipitated with Fn antibody, immunoprecipitates resolved by SDS-PAGE under reducing conditions, and detected by Western blotting with either Fn or UG antibody. The immunoprecipitates contain both Fn (lane 2, upper panel) and UG (lane 2, lower panel). Lanes 1 of both panels represent Fn and UG standards. (C) Equimolar concentrations of $^{125}$I-UG and Fn were incubated at 4° C. for 1 hour and the resulting complex was resolved by electropboresis on 6% non-reducing, non-denaturing polyacrylamide gels. Lane 1, Coomassie blue stained Fn-UG heteromer; lane 2, its autoradiogram. (D) Immunoprecipitation of plasma (18) from UG$^{+/+}$ and UG$^{-/-}$ mice with Fn-antibody and Western blotting with Fn and UG antibodies. Fn (upper panel); UG (lower panel). Std=standards for UG and Fn. (E) Affinity-crosslinkig, of $^{125}$I-Fn with unlabeled Fn in the absence (lane 2) and presence of varying amounts of UG (lanes 3–5). The intensity of the very high molecular weight, radioactive Fn band (lane 2) formed in the absence of UG is reduced in a dose-dependent manner. Lane 1, $^{125}$I-Fn with unlabeled Fn in the absence of UG and DSS. Open arrowhead=mulcimneric Fn; Lower thin arrow=220 kDa Fn. (F) Affinity-crosslinkingof $^{125}$I-collagen-I with unlabeled Fn in the absence (lare 3) and presence (lane 4) of UG. Lane 1, Coomassmie blue-stained collagen I; $\alpha_1=\alpha_1$, chain of collagen I and $\alpha_2=\alpha_2$ chain of collagen I. Lane 2, $^{125}$I-collagen I and unlabeled Fn in the absence of UG and DSS.

FIG. 6 Inhibition of Glomerular Fn-deposition, in vitro Matrix Assembly and Fibrillogenesis by UG. A. Kidney section of a wild-type mouse that received a mixture of equimolar concentrations of Fn and UG intravenously. B. UG$^{+/+}$ mouse that received the same dose of Fn as in (A) but without UG. C. Apparently healthy, UG$^{-/-}$ mouse receiving a mixture of Fn and UG. D. UG$^{-/-}$ receiving Fn alone (same dose as in C), but without UG; E. Fn-fibrillogenesis by cultured cells (29) grown in mdium supplemented with soluble hFn alone; F. a cell culture identical to the one in (E) which was fed with medium containing a mixture of equimolar concentrations of soluble hFn and UG. Magnification 40×. g=glomerulus.

DETAILED DESCRIPTION OF PREFERRED EMBODIMENTS

Figure 4A:
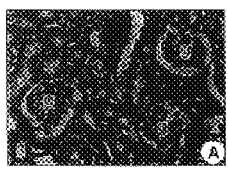
FIGS. 4A–4J compare histopathological analyses of kidney sections from normal versus $UG^{-/-}$ mice, showing abnormal parenchymal fibrosis and glomerular Fn deposition in the knockout mice only. These figures show severe renal glomerular disease in $UG^{-/-}$ mice. H & E staining of kidney sections from a $UG^{+/+}$ (A) and its $UG^{-/-}$ (B) littermate.
Figure 4B:
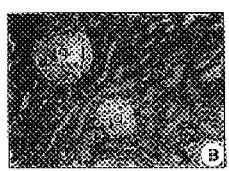
Figure 4C:
Figure 4D:

The method of the present invention, in one aspect, comprises administering to a mammal, which may be animal or human, suffering from an inflammatory or fibrotic condition, an effective amount of pure rhUG. The rhUG may be administered intravenously or, in the case of treatment of neonatal RDS/BPD and adult RDS, in the form of a semi-aerosol via the intratracheal tube.

By "pure rhUG" is meant: 1) that no other proteins are detectable in the rhUG preparation by SDS-PAGE, Western blot or immnunoprecipitation with anti-E. coli antibodies, or by analytical HPLC; 2) thlat no bacterial endotoxin is detectable by LAL test; 3) that no bacterial nucleic acid is detectable by Southern blot, ethidium bromide staining or by SYBR green fluorescence; and 4) that the rhUG has the correct molecular weight using mass spectral analysis. The rhUG typically has a purity of 98–100%.

The method of the invention is useful for the treatment of conditions characterized by a deficiency of UG. The invention is especially adapted for the treatment of pulmonary inflammatory conditions, for example neonatal respiratory distress syndrome (RDS) and bronchopulmonary dysplasia (BPD).

The method of the invention is useful for the treatment of conditions characterized by an elevation in serum PLA$_2$ activity, such as adult RDS (ARDS), septic shock, pancreatitis, collagen vascular diseases, rheumatoid arthritis, acute renal failure, and autoimmune uveitis.

The method of the invention is useful for the treatment of conditions characterized by local elevations in PLA$_2$ activity, such as neonatal RD S/B PD, ARDS, rheumatoid arthritis, asthma, peritonitis, glomerulopathies, including hereditary Fn-deposit glomerulonephritis, and autoimmune uveitis.

The method is also useful in the treatment of fibrotic conditions where deposition of fibronectin is a causative factor. Idiopathic pulmonary fibrosis, bleomycin lung, and cystic fibrosis are examples of pulmonary conditions which can be treated in accordance with the present invention. Glomerular nephropathy, particularly familial glomeruleropathy, characterized by Fn deposits in the kidneys, ultimately leading to renal failure, can also be treated with exogenous UG.

The invention also contemplates a method for treating or preventing an inflammatory or fibrotic condition characterized by a deficiency of endogenous finctional UG, which comprises administering to a patient in need of such treatment a compensating amount of rhUG. By the term "compensating amount" is meant an amount of rhUG required to bring the local pulmonary or systemic concentration of total UG (endogenous functional UG and rhUG) to within its normal range. More specifically, the normal range for local pulmonary concentration of endogenous functional UG is >50 micrograms UG/milligram albumin (Dhanireddy, et al. 1988; supra) or >500 micrograms/liter (Bernard, et al. 1992; supra). The normal range for serum UG concentration is >15 micrograms/liter (Bernard, et al. 1992: supra).

The compositions of the invention comprise rhUG in an amount effective to achieve the intended purpose, namely increased plasma or tissue levels of rhUG to produce the desired effect of selective inhibition of PLA$_2$s and reduced inflammation and/or binding of fibronectin to mitigate fibrotic conditions. The compositions comprise an effective amount of pure rhUG, prepared as described hereinafter, in association with a pharmaceutically acceptable carrier or diluent.

In a further aspect, the compositions of the invention comprise an effective amount of rhUG and lung surfactant, in association with a pharmaceutically acceptable carrier or diluent. Local intratracheal administration of rhUG to the lungs, sufficient for inhibition of PLA$_2$ activity and/or fibronectin deposition requires quantities of pure rhUG in the range of 0.2 µg/kg to 500 mg/kg of protein in single or multiple dosages. The rhUG is usually administered in an amount of a single bolus of 20 ng/kg to 500 mg/kg, in single or multiple doses, or as a continuous infusion of up to 10 grams.

RhUG may also be administered in conjunction with artificial lung surfactant, such as Survanta, via the intratracheal route. RhUG and Survanta (5 mls/kg) are co-administered and rhUG does not bind up surfactant, preventing it from functioning therapeutically. The lung surfactant is generally present in the composition an amount of about 10–90% by weight, more usually about 20–80% by weight. The surfactant, by virtue of its very low surface tension spreads out over the internal surface of the lungs, carrying the rhUG with it. Systemic administration of rhUG via intravenous injection, sufficient for inhibition of PLA$_2$ activity and/or fibronectin deposition, requires quantities of pure rhUG in the range of 0.5 µg to a continuous infusion of several grams of protein over an extended period of time (days.)

Suitable formulations for injection and semi-aerosol intratracheal delivery include aqueous solutions of rhUG optionally with viscosity modifiers and stabilizers.

The term "TLA$_2$ inhibiting effective amount" as used herein means the amount of rhUG which inhibits PLA$_2$ activity and which reduces or alleviates inflammation in the tissue or body of the patient. The term "fibronectin binding effective amount" means that amount of rhUG which binds fibronectin to reduce deposition thereof, and prevent or reduce fibrosis. The term "anti-inflammatory amount" as used herein means the amount which reduces or alleviates inflammation in the tissue or body.

Typically, the amount of rhUG administered to adults for the treatment of inflammatory and fibrotic conditions will be single boluses of 0.2 µg/kg to 500 mg/kg or up to several grams administered over an extended period of time. For neonates, in the treatment of neonatal RDS, the range will typically be 50 nanograms/kg to 100 mg/kg in single boluses or up to 10 grams administered continuously over an extended period of time. Effective and safe rates of continuous infusion are between 50 ng/kg/hour to 500 mg/kg/hour.

EXAMPLES

The invention will now be further described with reference to the following non-limiting examples. Parts and percentages are by weight unless otherwise stated.

Example 1

Production and Characterization of rhUG

Recombinant human UG is produced by the following procedures, and possesses a level of purity exceeding 99% such that it may be used according to the present invention to inhibit PLA$_2$ activity and reduce fibronectin deposition in vitro and in vivo.

Construction of Bacterial Gene for rhUG

A synthetic gene for human UG is assembled from oligonucleotides and cloned into pBR322 for DNA sequencing to confirm the sequence. Because native UG has a glutamic acid residue at its N-terminus, an initiator methionine will be added. Mantile et al (1993; supra) have previously shown that addition of Met-Ala-Ala (SEQ ID NO:5) at the N-terminus of recombinant hUG does not alter its activity as an inhibitor of PLA$_2$. Nor does a Met residue at the N-terminus (which allows bacterial translational initiation) effect is activity as a PCB-binding protein (Hard et al, 1996; supra). Bam H1 sticky ends are located at both ends of the annealed gene to facilitate cloning into the Bam H1 site of pBR322, which allows identification of clones by screening for sensitivity to tetracycline. Codon usage will be optimized for expression in bacteria according to Anderssen and Kurland (Codon Preferences in Free-living Microorganisms. Microbiological Reviews. 54:198–210 (1990)). Thus far, it has only been expressed from the human cDNA sequence with only moderate levels of protein expression and recovery achieved. The optimization of codon usage typically results in a higher translation efficiency and expression level. Oligos 1–4 represent the coding strand and 5–8 represent the complementary strand. Both sets are in order from 5' to 3', respectively, and are assembled as in FIG. 2.

Table of Oligonucleotides

5'-GATCCATGGAAATCTGCCCGTCTTTCCAGCGTG TTATCGAAAC CCTGCTGATGGACACCCCGTCC-3' (SEQ ID NO:6)

5'-AGCTACGAAGCAGCTATGGAACTGTTCTCTCC GGACCAGGA CATGCGTGAA GCAGGTGCT-3' (SEQ ID NO:7)

5'-CAGCTGAAGAAACTGGTTGACACCCTGCCGCA GAAACCGCGTG AATCCATCATAAACTG-3' (SEQ ID NO:8)

5'-ATGGAGAAGATCGCTCAGTCTAGCCTGTGCAA CTAAG-3' (SEQ ID NO:9)

5'-CTTAGTTGCACAGGCTAGACTGAGCGATCTTCT CCATCAGTTTG ATGATGGATTCACGCG-3' (SEQ ID NO:10)

5'-GTTTCTGCGGCAGGGTGTCAACCAGTTTCTTCA GCTGAGCACT GCTTCACGCATGTCCT-3' (SEQ ID NO:11)

5'-GGTCCGGAGAGAACAGTTCCATAGCTGCTTCG TAGCTGGACG GGGTGTCCATCAGCAGGG-3' (SEQ ID NO:12)

5'-TTTCGATAACACGCTGGAAAGACGGGCAGATT ITCCATGGATC-3' (SEQ ID NO:13)

Subcloning of Coding Sequence into Expression Vector

Oligonucleotides homologous to the 3' and 5' ends of the new gene are then used to amplify the gene from pBR322 by PCR and done it into pP$_L$-lambda. The cloning strategy, as well as a map of the expression vector is shown in FIG. 2. Restriction sites are incorporated into the ends of the flanking oligonucleotides to facilitate directional cloning of the gene into the vector.

Ligation mixtures are transformed into the first strain (NM4830-1 for pP$_L$-lambda) and plasmid-bearing colonies are selected with ampicilin. Transformants are initially screened with a quick PCR assay done on the bacterial colonies to determine insert size. The secondary screen is done in 10 ml bacterial cultures for expression of an induced protein of the appropriate size (10 kDa). Samples of whole cells, induced for expression of the uteroglobin, directly lysed in 2x gel loading buffer, are run on 16% Tris-glycine SDS-PAGE gels in a minigel apparatus. Plasmid DNA from clones that exhibit overexpressed induced UG is then prepared and the DNA sequence is verified. Both plasmid DNA and bacterial strains from positive clones are then frozen down and stored. Clones for expression are maintained on LB plates containing ampicillin. These are streaked weekly for up to 10 passages, after which a fresh streak is taken from a frozen seed vial for serial culture, to insure strain authenticity.

Bacterial Host Strain Construction

An *E. coli* host strain is constructed for expression of rhUG from the heat-inducible promoter, P$_L$, from a bacteriophage lambda. This promoter requires the lambda repressor, cI, in order to remain inactive until the desired time of expression. The temperature sensitive cI protein (mutant cI$_{453}$) binds to the P$_L$ promoter when the temperature is 32° C. or less (Sambrook, et al, 1989). When the temperature is rapidly elevated to 42° C. (i.e., less than 15°), the cI$_{453}$ repressor undergoes a conformational switch and no longer binds the P$_L$ promoter sequence. This results in overexpression of the rhUG gene. The bacterial host strain is derived from wild type *E. coli*, strain W3110, obtained from the ATCC. Wild type strains are generally regarded as more robust than typical research cloning strains and are preferred for protein production. A lysogen of this strain is constructed using a cI$_{453}$, Xis- mutant of lamba phage, also obtained from the ATCC. This strain constitutively expresses the cI$_{453}$ repressor. Since the lysogen is Xis-, the prophage cannot excise itself from the host chromosome, preventing replication of the phage when expression of the protein is induced. This host strain, W3110λcI$_{453}$, is transformed with the expression vector and maintained as described previously. Individual colony transformants are also screened for expression as described.

Expression of rhUG

Clones selected for expression of rhUG are inoculated from colonies on solid media into 50 mL of broth and shaken overnight. This starter culture is used to inoculate 250 ml rich media containing ampicillin at 100 micrograms per mL in shaker flasks. These cultures are grown at 32° C. until they reach an optical density of 0.5 at 600 nm. Expression of rhUG is then induced with a heat shift to 42° C. The culture is shaken for an additional 2–4 hours at 42° C. The cells are then harvested by centrifugation, washed once with PBS, and stored at −20° C. as a frozen cell pellet until analyzed. These cells pellets are used in the initial stages of the development of a purification process.

Storage and Stability of Expression Strains

Up to four strains that overproduce large quantities of active rhUG are cultured, without expression. Culture conditions for preparation of seed stock are slightly different from those used in protein expression with the same strains, due to the different objectives for growing the cultures. Seed stock cultures are grown under conditions that minimize expression and enhance stability, ie. the temperature is kept below 30° C. and media is minimal with appropriate supplements. Seed stock material is grown to early stationary phase in ten liter batches in Microferm fermenters (New Brunswick), gently pelleted and frozen down (−70° C.) in 4% glycerol in aliquots equivalent to 200 mL of culture. Likewise, lyophilized material is generated from several liters worth of bacterial culture for storage. Stored bacteria are evaluated for stability of plasmid, DNA sequence and expression level at six month intervals.

Fermentation Optimization

Of the four expression strains selected for storage, the best two are selected for fermentation optimization, based on protein analysis, at the 2 liter scale. The goal is to maintain a high, specific yield (percent rhUG versus total soluble protein) while maximizing biomass. This begins with fermentations to gauge the maximum biomass achievable (maximum $OD_{600}$ and wet weight cell paste) in both minimal media, supplemented with glucose, and in rich media at 37° C., followed by a time course of the expression to determine peak uteroglobin production as a function of $OD_{600}$ following induction.

Information generated by these two sets of experiments provide the three parameters necessary to initiate preliminary production runs:

1) Use of rich versus minimal media. If comparable results for specific yield and maximum biomass can be obtained, then minimal media is preferable due to materials cost considerations. The time course for a minimal versus a rich media run must also be considered, since doubling time is typically lower in minimal media and the cost of labor on off-shifts is high. Note that for the number of potential applications for rhUG, a large quantity (kilograms per year) may eventually be required.

2) The point at which induction begins is approximately two doubling times prior to entry into stationary phase. The maximal doubling rate is mid-late log phase and is a criterion of maximizing heterologous protein expression.

3) The expression time course determines the time post-induction at which the culture must be harvested. In rich media, rhUG accumulation is very rapid (up to 50% total protein in 2–4 hours), while in supplemented minimal media, protein accumulation requires several hours (up to 40% of the total protein in 12–18 hours).

The stability of the expression vector is an important issue in the validation of the expression system. It is routinely monitored by comparing cfu's of cells plated from the fermentation inoculum and the harvest, on selective versus non-selective media. Once parameters are established for the initial production runs, stability is initially validated by platings from timepoints in the fermentation as well as by DNA sequencing of the UG gene in plasmids extracted from cells at the beginning and end of the fermentation to verify that no changes have occurred.

Purification of UG; Preparation of Extracts

RhUG will be purified largely according to Mantile et al, 1993; supra and to Miele et al, 1990; supra, with the following modifications. Frozen cell pellets are thawed rapidly and resuspended in approximately 2 mLs of ice cold hypotonic lysis buffer (50 mM NaPO4, pH 10) per gram of wet cell paste. (The use of protease inhibitors (PMSF, leupeptin, and soybean trypsin inhibitor) is necessary in the early stages but may eventually be eliminated). The cell suspension is subjected to 3 freeze-thaw cycle, alternating between a dry ice ethanol bath and a 65° C. for 5–10 minutes and then centrifuged at 30×g for 20 minutes. Heating the lysate at this point precipitates the bulk of the host proteins and inactivates proteases. The supernatant containing the rhUG is decanted to a clean tube and the pellet is discarded. Except for the heat step, all materials and samples are kept ice cold. RhUG extracts and fractions are examined by SDS-PAGE (16% Tris-glycine), by protein assay (Pierce BCA kit), and by $PLA_2$ inhibition activity in vitro according to the manufacturers (EIA, Cayman Chemicals), as needed, to evaluate lysate fractionation steps, as well as to evaluate chromatography, filtration and other purification steps.

Filtration and Chromatography

The purification of rhUG is monitored for recovery of bioactive material after each step in the process. As described above for lysates, SDS-PAGE, protein assay and $PLA_2$ inhibition assay are used to evaluate steps in the process. Because the end product is to be used in humans, Tris, EDTA and other unnatural components are eliminated from buffers for purification. The introduction of a cost-effective heat step eliminates extra chromatograph steps downstream. Special consideration is also given to non-protein contaminants. The removal of endotoxin and DNA is facilitated by the use of new filtration step.

Clarified bacterial lysates typically have a pH close to neutrality, presumably because the weak buffering strength of the dilute buffer system is overwhelmed by cellular contents once efficient lysis is achieved. The pH of the sample buffer will be dropped to 4.2 with ammonium acetate slowly, with stirring in the cold. RhUG is known to be stable at low pH (Andersson, 1994; supra, Miele, L., et al. High level expression in E. coli of a dimeric, eukaryotic protein with two disulfide bridges under the control of phage T7 promoter. J. Biol. Chem. 265:6427–6435 91990)). The sample is then passed over a Sartobind filter (Sartorius Corp). At low pH, endotoxin and DNA bind with high efficiency to this membrane and are effectively removed. The UG sample is placed on a CM-Sepharose column equilibrated with 25 mM ammonium acetate, pH 4.2. (Column sizes are determined based on protein content in the sample, estimated rhUG content, and sample volume). RhUG binds to the column under these conditions. It is eluted with a linear gradient of 25 mM ammonium acetate, pH 4.2, and 120 mM ammonium acetate, pH 6.0 (Miele, L., et al, 1990; supra). This process is converted to a step gradient when a reproducible elution profile is obtained. If a second chromatography step is necessary, sample fractions are pooled and concentrated using a YM-2 membrane (Amicon). The sample is then passed over a Sephadex G-75 column equilibrated in 20 mM potassium phosphate, pH 7.2. RhUG fractions are pooled and concentrated again using the YM-2 membrane. The final sample is characterized for activity and concentration. Some aliquots of rhUG are lyophilized and stored at −70° C. with dessicant, others are stored in PBS at 4° C.

Molecular Analysis of rhUG

Several methods are used to characterize the final rhUG preparation. The purified dimeric protein is a single band of about 10 kDa on a non-reducing SDS-PAGE gel that collapses to a single 6 kDa band on a reducing SDS-PAGE gel, and is recognized by anti-uteroglobin antibodies in Western blots. Only the dimeric form is active in inhibiting $PLA_2$ in vitro. $PLA_2$ activity is measured with an EIA kit (Cayman Chemicals). The activity of each preparation of recombinant human protein is compared to native UG preparation derived from human urine, on an activity versus weight basis (specific activity). Homogeneity is evaluated using analytical HPLC (C-18 reverse phase, 5 micron pore size. TFA:acetonitrile gradient) versus authentic human UG. MALDI-TOF mass spectral analysis is done (M-Scan, Inc.) to verify molecular weight. Amino acid content analysis is done to verify identity (Peptide Technologies, Inc.) N-terminal amino acid sequencing is also done to verify authenticity.

Contaminant Analysis

Testing for E. coli host proteins, endotoxin, and residual bacterial DNA is done. Elimination of host proteins is largely accomplished by the time the protein appears as a single band on an overloaded silver-stained SDA-PAGE gel, and as a single HPLC peak. However, this is verified in a more sensitive immunoassay (Western dot blot) using polyclonal antibodies generated against E. coli proteins. The levels of DNA and endotoxin contaminants are characterized by the use of a chromogenic LAL assay kit (Becton-Dickenson) and SYBR green dye kit (Molecular Probes), measured in the clarified lysate, before and after the filtration step, and in the final sample. Pure rhUG contains none of these contaminants in detectable quantities, reflecting at least 99% purity.

Stability Testing of rhUG

Studies on the stability of rhUG, as a lyophil, in a frozen liquid at −20° C. and −70° C., and as a liquid suspension kept in the refrigerator and at room temperature are done. The preferred form for cost-effective storage is in liquid room temperature, however, this may not be practical. Purified rhUG preparations continue to be monitored for stability in these forms by testing for $PLA_2$ inhibition activity over time. Initial time points for resuspended forms were daily for the first week, then twice per week for the first month. The lyophilized samples are stable for at least two years (A.B. Mukherjee, unpublished data), therefore, stability testing was done biweekly for the first month, then monthly for the first year. All rhUG preparations have been stable thus far (A.B. Mukhexjee, personal communication).

Example 2

In Vivo Experiments

One male and one female of the species *P. cyanocephalus*, weighing approximately 400 grams each were delivered by C-section at 142 days of gestation. This is an established model of RDS (Coalson, J. J., et al. Baboon Model of BPD. II: Pathologic features. Exp. Mol. Pathol. 37: 355–350 (1982)).

After delivery, the infants were anesthetized with ketamine (10 mg/kg) and intubated with a 2.5 mm diameter endotracheal tube. Blood gases and pressure were monitored via an arterial line placed by percutaneous injection into the radial artery. A deep venous line was placed percutaneously into this saphenous vein through which fluids and drug were administered. Animals were maintained on servo-controlled infrared warmers and ventilated with a standard time-cycled, pressure-regulated ventilator with humidifiers maintained at 36–37° C. Initial setting were $FiO_2$ 1.0, rate 40/min., I/E ratio 1:1.5, positive end expiratory pressure (PHEP) at 4 cm $H_2O$, and peak inspiratory pressure (PIP) as required for adequate chest excursion. $FiO_2$ was kept at 1.0 and PIP was regulated to maintain $PaCO_2$ at 40±10 torr. Blood gases, hematocrit, electrolytes, prothrombin time, partial thromboplastin time and dextrostix were monitored hourly. Blood drawn for studies was replaced volumetrically with heparinized adult baboon blood. Intravenous fluids were administered with electrolytes at 10 cc/kg/hr and were increased as needed when heart rate exceeded 180 beats/min. Sodium bicarbonate (2 meq/kg) was administered when the base deficit exceeded −10. Ampicillin (50 mg/kg/day in two divided doses) and Gentamicin (5 mg/kg/day into two divided doses was given continuously for the duration of the experiment.

One animal received surfactant plus PBS (treatment no. 1), and the second animal (treatment no. 2) received surfactant plus two doses of 1 mg/kg of rhUG. The surfactant used was Survanta (Abbott), a surfactant preparation derived from bovine lung tissue, containing surfactant apoproteins B and C in addition to phospholipids. The first dose was given with the surfactant and the second administered four hours after the first. The animals were monitored for arterial blood gases, electrolytes and EKG. They were sacrificed 50 hours after the initiation of surfactant therapy. The lungs were lavaged at 24 and 48 hours with PBS containing protease inhibitors (PMSF, 10 μg/ml leupeptin, 10 μg/ml of pepstatin and bacitracin). They were frozen at −80° C. until assayed for $PLA_2$ activity. Total proteins were determined by Bradford method (BioRad). The $PLA_2$ activity in the lung lavages were measured according to Levin et al. (1986; supra) and are presented in the following Table.

TABLE

| Treatment # | Time | Lung lavage $PLA_2$ activity (ccpm/10 μg protein |
|---|---|---|
| 1 | 24 hr | 3030 |
|   | 48 hr | 2607 |
| 2 | 24 hr | 1739 |
|   | 48 hr | 996 |

The data given above are the mean of two determinations. The results show that endotracheal administration of rhUG inhibits $PLA_2$ in vivo. The animals which received surfactant and rhUG had an appreciably lower $PLA_2$ activity in their lung lavage fluid compared with the animals that received surfactant without rhUG. The data confirms that administration of rhUG in conjunction with surfactant is beneficial in protecting surfactant phospholipids.

Example 3

Inhibition of Hydrolysis of Artificial Surfactant by Soluble $PLA_2$s in vitro

RhUG inhibits hydrolysis of artificial surfactant by soluble $PLA_2$s in vitro. Survanta is an artificial surfactant derived from bovine lung and is used to treat preterm neonates with RDS and adults with RDS (ARDS). Hydrolysis of Survanta by a Group I soluble $PLA_2$, i.e. porcine, pancreatic $PLA_2$ (Sigma) is characterized by its ability to compete as a substrate with a fluorescent phosphatidylcholine substrate (Cayman Chemicals), generating arachidonic acid as a product.

Survanta is a substrate for in vitro degradation by Group I soluble $PLA_2$s. Survanta is rapidly degraded in vitro by $PLA_2$s found in the extracellular fluids of a human lung. RhUG inhibits degradation of Survanta in vitro.

Example 4

Construction of UG Knockout Mouse.

A transgenic UG knockout mouse was created for the purpose of determining the role of UG in mammalian physiology, as well as to generate a model for UG as a therapeutic in several inflammatory clinical conditions. The first step was to construct an appropriate DNA vector with which to target and interrupt the endogenous murine UG gene. The 3.2 kb BainHI-EcoRI DNA fragment containing exon 3 and flanking sequences of the UG gene from the 129/SVJ mouse strain (Ray, 1993) were subcloned into the corresponding sites of the pPNW vector as described in Lei et al (1996). A 0.9 kb fragment containing part of exon 2 and its upstream sequence was amplified by PCR (with primers Primer-L (from Intron 1): 5'-TTC CAA GGC AGA ACA TTT GAG AC-3' (SEQ ID NO:14); Primer-R (from Exon 2): 5'-TCT GAG CCA GGG TTG AAA GG C-3'(SEQ ID NO:18)) (SEQ ID NO:15) with NotI and XhoI restriction sites engineered into the termini for directional subcloning into the gene targeting vector. In this construct, 79 bp of Exon 2 encoding 27 amino acids were deleted. The PCR fragment was placed upstream of the gene encoding neomycin resistance in pPNW, generating the gene targeting vector, PNWUG. The vector is shown in FIG. 3A, in which the PGK-neo cassette interrupts the UG gene, disrupting the protein coding sequence.

The pPNWUG gene targeting vector was linearized with NotI and electroporated into ES $R_1$ cells according to Nagy, A., Rossant, J., Nagy, R., Abramow-Newerly, W., and J. C. Roder. PNAS 90:8424 (1993). Gancyclovir and G-418 selection of the electroporated cells yielded 156 clones.

Southern (DNA) blot analysis identified a 5.1 kb HindIII fragment of the wild-type UG allele and an additional 8.2 kb HindIII fragment resulting from homologous recombination in three out of the 156 clones, shown in FIG. 3B. These E'S R1 clones were injected into C57BL/6 blastocysts according to M. R. Capecchi, Science 244: 1288 (1989). Two different lines of mice, descended from different chimeric founders, were generated. Heterozygous offspring (UG$^{+/-}$) carrying the targeted UG gene locus were mated and the genotypes of the progeny were analyzed by PCR shown in FIG. 3C, as well as Southern blot, shown in FIG. 3D.

Example 5

Verification of UG Gene Knockout and Absence of UG Protein

In order to verify that the homozygous knockout mice (UG$^{-/-}$) did not possess any detectable UG, the UG gene-targeted mice were tested for expression of UG-MRNA and UG protein in several organs including the lungs. An experimental protocol was approved by the institutional animal care and use committee. Total RNAs were isolated from different organs of UG$^{+/+}$, UG$^{+/-}$, and UG$^{-/-}$ mice. The reverse transcribed-polymerase chain reaction (RT-PCR) was used to detect UG-MRNA. Target molecules were reverse transcribed using a UG-specific primer, mPr (5'-ATC TTG CTT ACA CAG AGG ACT TG-3')(SEQ ID NO:16), and the cDNA generated was amplified using PCR primers mPr and mPl (5'-ATC GCC ATC ACA ATC ACT GT-3') (SEQ ID NO:17). The PCR product was hybridized with an oligonucleotide probe, mPp (5'-ATC AGA GTC TGG TTA TGT GGC ATC C-3')(SEQ ID NO:18) derived from exon-2 of the UG gene sequence. The primers and the probe used in mouse GAPDH RT-PCR are as follows: mGAPDH-r (5'-GGC ATC GAA GGT GGA AGA GT-3')(SEQ ID NO:19); mGAPDH-l (5'-ATG GCC TTC CGT GTT CCT AC-3') (SEQ ID NO:20); mGAPDH-p (5'-GAA GGT GGT GAA GCA GGC ATC TGA GG-3')(SEQ ID NO:21). FIG. 3E shows that UG-mRNA was detected in the lungs of UG$^{+/+}$, and UG$^{+/-}$, but not UG$^{-/-}$ mice. Similar data (not shown) show that UG-mRNA is not present in either the prostate or uteri of UG$^{-/-}$ mice, but is present in the mice with an intact UG gene.

Immunoprecipitation and Western blot analyses of UG protein in the lungs yielded similar corroborative results, shown in FIG. 3F. Tissue lysates from the kidneys, liver, and the lungs of the UG$^{+/+}$ and UG$^{-/-}$ mice were prepared by homogenizing in a buffer (10 mM Tris-HCl, pH 7.5, 1% Triton X-100, 0.2% deoxycholate, 150 mM NaCl, 5 mM EDTA) containing 2 mM phenylmethylsulfonyl fluoride and 20 μg/mL each of aprotinin, leupeptin, and pepstatin A. The homogenates were centrifuged at 17,500×g for 30 min at 4° C. and immunoprecipitated as described (E. Harlow and D. Lane, Antibodies; a laboratory manual, 1st Ed. Cold Spring Harbor Laboratory Press, Cold Spring Harbor, N.Y., 1988) by incubating tissue lysates or plasma proteins (1 mg/mL) with rabbit antibody against murine Fn (1:100 dilution). Co-immunoprecipitation of purified murine Fn and recombinant human UG (Mantile, G, et al., J. Biol. Chem. 267: 20343 (1993) was performed by incubating equimolar concentrations of Fn with UG in the presence of 10% glycerol, 50 mM Tris-HCl, pH 7.5, 250 mM NaCl, 4.3 mM sodium phosphate at 4° C. for 1 hr., followed by adding murine Fn antibody (1:100 dilution). Equal amounts of extracted tissue proteins (30 μg) or immunoprecipitates were resolved either on 4–20% or 6% SDS-polyacrylamide gels under reducing conditions, followed by Western blotting with rabbit antibodies against either murine Fn (1:2000 dilution) or UG (1:2000 dilution). No UG was detected in tissues or fluids from the UG$^{-/-}$ mice, while tissues from UG$^{+/+}$ and UG$^{+/-}$ mice did contain the UG protein.

Finally, histopathological analyses of the lungs of UG$^{-/-}$, only, lacked UG-specific immunostaining in bronchiolar epithelial cells. Lung tissues from UG$^{-/-}$, UG$^{+/-}$ and UG$^{+/+}$ mice were fixed in Bouin's fluid or in 10% neutral buffered formalin fixatives, embedded in paraffin and sectioned at 4–6 microns. They were stained with hemotoxylin and eosin (H & E). Selected tissues were stained by Masson's trichrome method for collagen detection, PTAH for fibrin, or Congo Red for amyloid protein. For immunohistochemical detection of UG and Fn, the Vectastain rabbit Elite ABC kit (Vector Laboratories) was used. The rabbit antibody (CytImmune) to mouse UG (mUG) was raised by using a synthetic peptide (Peptide Technologies, Inc.) corresponding to mUG amino acid sequence (Lys28 to Thr49, specifically KPFNPGSDLQNAGTQLKRLVDT). (SEQ ID NO:22) the rabbit antibody to mouse Fn (GIBCO BRL) was used at a dilution of 1:1000, and the antibody to mUG was used at 1:500.

These three sets of results confirm that the homozygous UG knockout mouse, UG$^{-/-}$, lacks UG protein, or any detectable piece of the protein.

Example 6

Phenotype of UG Knockout Mouse

Of the 179 mice born to crosses of UG$^{+/-}$ mice, 46 (26%) were of the +/+, 90 (50%) of the +/− and 43 (24%) of the UG$^{-/-}$ genotype, indicating that the disrupted UG locus is inherited in a Mendelian fashion and that UG$^{+/+}$, UG$^{+/-}$, and UG$^{-/-}$ mice were equally viable at birth. However, UG$^{-/-}$ mice exhibited a novel phenotype in which they developed a progressive illness characterized by cachexia, heavy proteinuria, and hypocalcemia associated with profound weight loss. Proteinuria is a condition in which abnormally high levels of albumin and other serum proteins are excreted in the urine. It is indicative of glomerular dysfunction and renal failure. Histopathological examination of the kidneys of affected animals (as described above for lungs) revealed the fulminant renal glomerular disease shown in FIG. 4. Compared with the glomeruli of the UG$^{+/+}$ mice, those of UG$^{-/-}$ mice were hypocellular and had massive eosinophilic proteinaceous deposits. The time course of the fatal renal disease in UG$^{-/-}$ mice was either early onset (4–5 week period) or late onset (10 month period). Those UG$^{-/-}$ mice that initially appeared healthy at 4 weeks of age had focal glomerular deposits at two months of age. At about 10 months, these mice had extreme cachexia similar to that of the mice dying of early onset disease. Heterozygotes had a milder form of the renal disease observed in UG$^{-/-}$ mice. Histopathology of the kidneys of mice with late onset disease showed not only severe glomerularopathy as in the early onset disease, but also had marked fibrosis of the renal parenchyma and tubular hyperplasia (see FIG. 4). Although the predominant pathology in the UG$^{-/-}$ mice was found in the kidneys, histopathological studies also uncovered occasional focal areas of necrosis in the pancreas which appeared to be vascular oriented. Moreover, focal areas in the thymus and in the spleen structures suggestive of apoptotic bodies were also found. Interestingly, the pancreas expresses the UG gene, and this organ is also a rich source of group-I extracellular PLA$_2$; since this is primarily a digestive enzyme, its activation may cause tissue injury.

Because UG has been reported to have immunomodulatory and anti-inflammatory properties and because reactive amyloidosis is known to occur in response to inflammation, it was likely that the glomerular deposits in the UG-null mice were amyloid proteins. Reactive amyloidosis is characterized by the deposition of amyloid protein and immune complexes. The identity of the renal deposits in the $UG^{-/-}$ mice was established by immunohistochemistry of kidney sections. Kidney sections from $UG^{-/-}$ and $UG^{+/+}$ mice were stained with Congo red and examined under the polarized light. Amyloid proteins yield a positive birefringence in this test; however, the glomeruli of $UG^{-/-}$ mice were clearly negative. Immunofluorescence studies for the presence of IgA, IgG or IgM-immunocomplexes in the glomeruli of $UG^{-/-}$ mice and immunohistochemical analyses for the presence of major amyloid proteins were also negative. Thus, the glomerular deposits of $UG^{-/-}$ mice contained neither amyloid proteins nor immunocomplexes, and therefore, do not appear to be the result of an inflammatory response.

Example 7
Detection of Fn and Collagen in $UG^{-/-}$ Kidneys

Figure 4E:
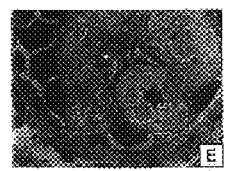
Figure 4F:
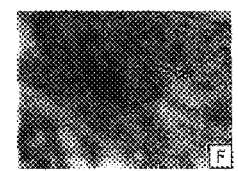
Figure 4G:
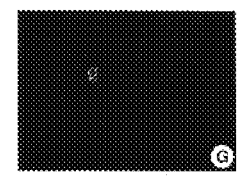

We next examined the kidney deposits of $UG^{-/-}$ mice by transmission electron microscopy to elucidate their structure and morphology. A kidney from a $UG^{-/-}$ mouse, with glomerular lesion, was fixed in formalin and embedded in epoxy resin. Thin sections were stained with uranyl acetate and lead citrate for examination under the electron microscope. Photomicrographs were taken either at 6000× or at 60,000×. The deposits contained primarily two types of fibrillar structures: one type of long and striated fibrils which are relatively infrequent, the other short and diffuse which are more abundant (FIGS. 4E and F). Because ECM proteins, such as collagen and fibronectin, produce similar fibrillar structures, the glomerular deposits in UG mice may contain these proteins.

Figure 4H:
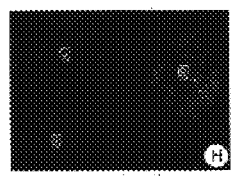
Figure 4I:
Figure 4J:

The glomerular deposits were next analyzed by immunofluorecence using murine Fn antibody. Formalin-fixed tissue sections were used for immunofluorescence as previously described (5) using a rabbit anti-mouse Fn and FITC-conjugated goat anti-rabbit IgG. Similarly, immunofluoresence studies using antibodies specific for Fn, collagen I and III, vitronectin, laminin and osteopontin were also done. Epifluorescence was photographed using a Zeiss Axiophot microscope. Fn-specific immunofluorescence in the renal glomeruli of wild-type mice was virtually undetectable (FIG. 4G), that in the glomeruli of $UG^{-/-}$ littermates was intense (FIG. 4H). When Masson's trichrome staining was used, the glomeruli of $UG^{+/+}$ mice were negative (FIG. 4I) and those of $UG^{-/-}$ (FIG. 4J) mice were positive, suggesting the presence of collagen in the glomerular deposits. Immunofluoresence, using collagen I and collagen III-specific antibodies confirmed these results. Because Fn is known to interact with other ECM proteins, we also tested for the presence of laminin, vitronectin and osteopontin in the glomeruli of $UG^{+/+}$ and UfG mice by immunohistochemistry, the results of which were negative.

Example 8
Kidneys of $UG^{-/-}$ Mice do not Overproduce Fn

Figure 5A:
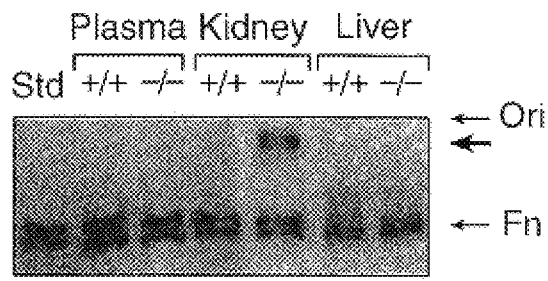
FIG. 5 A shows the presence of Fn aggregates only in the kidneys of the UG$^{-/-}$ mice by immunoprecipitation (18) and Western blotting of Fn from plasma, kidney and liver of UG$^{+/+}$ and UG$^{-/-}$ mice; a multimeric Fn band (bold arrow) was detected only in the kidney lysates of UG$^{-/-}$ mice.
FIGS. 5B and 5C show the formation of UG-Fn complexes in vitro; equimolar concentrations of UG and Fn were incubated, immunoprecipitated with Fn antibody, immunoprecipitates resolved by SDS-PAGE under reducing conditions, and detected by Western blotting with either Fn or UG antibody; the immunoprecipitates contain both Fn (lane 2, upper panel) and UG (lane 2, lower panel); lanes 1 of both panels represent Fn and UG standards.
FIG. 5D shows the presence of UG-Fn complexes in the plasma of normal but not UG$^{-/-}$ mice immunoprecipitation of plasma (18) from UG$^{+/+}$ and UG$^{-/-}$ mice with Fn-antibody and Western blotting with Fn and UG antibodies (Fn (upper panel), UG (lower panel), Std=standards for UG and Fn)
FIG. 5E shows the dose-dependent inhibition of Fn self-aggregation by UG in vitro using affinity-crosslinking of $^{125}$I-Fn with unlabeled Fn in the absence (lane 2) and presence of varying amounts of UG (lanes 3–5); the intensity of the very high molecular weight, radioactive Fn band (lane 2) formed in the absence of UG is reduced in a dose-dependent manner (lane 1, $^{125}$I-Fn with unlabeled Fn in the absence of UG and DSS; open arrowhead=multimeric Fn; lower thin arrow=220 kDa Fn)
FIG. 5F shows the inhibition of Fn-collagen complex formation by UG affinity-crosslinking of $^{125}$I-collagen-I with unlabeled Fn in the absence (lane 3) and presence (lane 4) of UG (lane 1, Coomassie blue-stained collagen I; $\alpha^1=\alpha^1$ chain of collagen I and $\alpha^2=\alpha^2$ chain of collagen I; lane 2, $^{125}$I-collagen I and unlabeled Fn in the absence of UG and DSS)

In order to determine whether excessive production of Fn may account for its deposition in the renal glomeruli, we assessed the relative amount of Fn-mRNA in the kidneys, lungs, and the liver of $UG^{-/-}$ and $UG^{+/+}$ mice by RT-PCR and densitometry. The results indicate that relative amounts of Fn-mRNA were essentially identical in both $UG^{+/+}$ and $UG^{-/-}$ animals. Thus, over-production of Fn-mRNA was not a likely cause of Fn-deposition in the glomeruli of $UG^{-/-}$ mice. We then compared the Fn-protein in the plasma, kidneys, and the liver of $UG^{-/-}$ and $UG^{+/+}$ mice by SDS-PAGE under reducing conditions, and Western blotting. In the plasma, kidneys and the liver of wild-type mice only 220-kD Fn species could be detected; however, whereas the plasma and the liver lysate of $UG^{-/-}$ mice had the 220-kD Fn band, the kidney lysates contained another distinct, covalently linked, multimeric Fn-band (FIG. 5A).

Example 9
Elevated Serum $PLA_2$ Activity in $UG^{-/-}$ mice

Based upon current concepts, critical initial steps in Fn matrix-assembly and fibrilogenesis, at least on the cell surface, are thought to involve integrin activation and Fn self-aggregation (E. Ruoslahti, Ann. Rev. Biochem. 57, 375 (1988); R. O. Hynes, Fibronectins. New York: Springer-Verlag (1990); M. A. Chernousov, F. J. Fogarty, V. E. Koteliansky and D. F. Mosher, D. F. J. Biol. Chem. 266, 10851 (1991); Q. Zhang, W. J. Checovich, D. M. Peters, R. M. Albrecht, and D. F. Mosher, J. Cell Biol. 127, 1447 (1994); C. Wu, V. M. Keivens, T. E. O'Toole, J. A. McDonald and M. H. Ginsberg, Cell, 83, 715 (1995), Q. Zhang and D. F. Mosher,J. Biol. Chem. 271, 33284 (1996). Because UG is a potent inhibitor of soluble phospholipase $A_2$ ($sPLA_2$) (Mantile et al. 1993; supra), a key enzyme in the inflammatory pathway, the lack of UG in $UG^{-/-}$ mice may contribute to the development of glomerulonephritis, an inflammatory renal disease (W. A. Border and E. Ruoslahti, J. Clin. Invest. 90, 1 (1992)). Moreover, lysophosphatidic acid (LPA), a byproduct of $PLA_2$ hydrolysis of phosphatidic acid, causes integrin activation, Fn matrix assembly and fibrilogenesis (E. Ruoslahti, Ann. Rev. Biochem. 57,375 (1988); R. O. Hynes, Fibronectins. New York: Springer-Verlag (1990); M. A. Chernousov, F. J. Fogarty, V. E. Koteliansky and D. F. Mosher, D. F. J. Biol. Chem. 266, 10851 (1991); Q. Zhang, W. J. Checovich, D. M. Peters, R. M. Albrecht, and D. F. Mosher, J. Cell Biol. 127, 1447 (1994); C. Wu, V. M. Keivens, T. E. O'Toole, J. A. McDonald and M. H. Ginsberg, Cell, 83, 715 (1995), Q. Zhang and D. F. Mosher,J. Biol. Chem. 271, 33284 (1996). Thus, we measured $PLA_2$ activity in the serum of age, sex and weightmatched $UG^{+/+}$ (n=3) and $UG^{-/-}$ mice (n=3). The animals were sacrificed and serum $PLA_2$ activities of each sample were measured in triplicate using a $PLA_2$-assay kit (Caymen Chemical) according to the instructions of the manufacturer. Protein concentrations in the sera were determined by Bradford assay (Bio Rad) and specific activities of $PLA_2$ were calculated. The specific activities ($\mu$mol/min/mg protein) of serum $PLA_2$ of $UG^{-/-}$ mice [36+3.3 (SEM)] were significantly higher (p<0.05) than those of $UG^{+/+}$ mice [18+2.8 (SEM)]. These results raised the possibility that higher $PLA_2$ activity may lead to increased LPA production and consequently promote integrin activation and Fn-self aggregation in $UG^{-/-}$ mice.

Example 10
Interaction of UG and Fibronectin in vitro

Figure 5B:
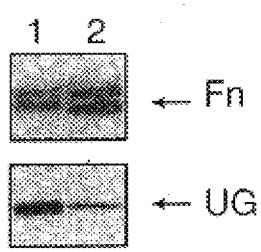
Figure 5C:
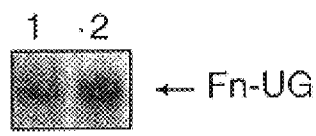
Figure 5D:
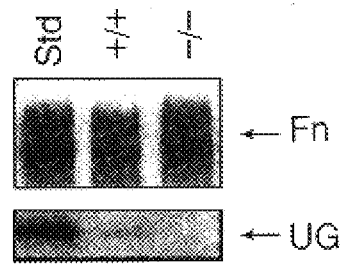

To further understand how UG may prevent Fn self assembly, the ability of UG to disrupt Fn—Fn interaction in vitro was determined. Equimolar concentrations of UG and Fn were incubated to allow any protein binding or other interactions, then immunoprecipitated with Fn-antibody, and the immunoprecipitates were resolved by SDS-PAGE under reducing conditions. Western blotting, as previously described, with either Fn or UG antibody detected each protein, respectively. The results show that fibronectin co-immunoprecipitated with UG (FIG. 5B). To confirm these results, the $^{125}$I-UG was incubated with Fn and the complexes resolved by electrophoresis, using a 6% polyacrylamide gel under non-denaturing and non-reducing conditions (FIG. 5C). Detection of a Fn-UG heteromer in the autoradiogram (lane 2) showed that soluble Fn interacts with UG in vitro. To ascertain whether Fn-UG heteromerization takes place in vivo, plasma of UG$^{+/+}$ and UG$^{-/-}$ mice was immunoprecipitated with a murine Fn antibody that does not crossreact with UG (FIG. 5D). Anti-murine Fn antibody co-precipitated both Fn and UG from the plasma of UG$^{+/+}$, but not from UG$^{-/-}$ mice, suggesting that Fn-UG heteromers are present in the plasma of UG$^{+/+}$ mice. Therefore, the Fn-UG complex is not simply an artifact formed in vitro but occurs naturally in the serum.

Figure 5E:
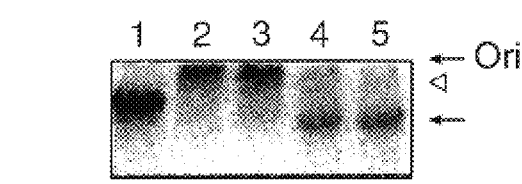

To determine the specificity and affinity of UG binding to Fn, we incubated $^{125}$I-Fn with unlabeled Fn in the presence and absence of UG. Any complexes were affinity-crosslinked with disuccinimidyl suberate (DSS). Using 24-well plates coated with hFn (Collaborative Biomedical Products), 3 µl of $^{125}$I-Fn (Sp. Act. 6 mCi/mg: ICN Biomedicals) was incubated in the absence and presence of either UG or Fn ($10^{-12}$–$10^{-6}$ M) in 500 µl HBSS at room temperature for 2 hr. SDS-PAGE and Western blotting of all Fn with UG antibody failed to detect any UG contamination. The radiolabeled complex was washed twice with PBS, solubilized in 1 N NaOH, neutralized with 1 N HCl, and radioactivity was measured by a gamma counter. In a separate experiment $^{125}$I-hFn (3 µl) was incubated with 20 µl (1 mg/ml) of mouse Fn in 40 µl of HBSS, pH 7.6 in the absence or presence of increasing concentrations of reduced UG (5–500 µg) at room temperature for 2 hours. The samples were crosslinked with 0.20 mM DSS at room temperature for 20 min., boiled in SDS-sample buffer for 5 min., electrophoresed on 4–20% SDS-polyacrylamide gel and autoradiographed. In the absence of UG, $^{125}$I-Fn formed a high molecular weight, radioactive complex with unlabeled Fn, but in the presence of UG the formation of Fn—Fn aggregates was inhibited in a manner dependent upon the UG concentration (FIG. 5E).

Figure 5F:
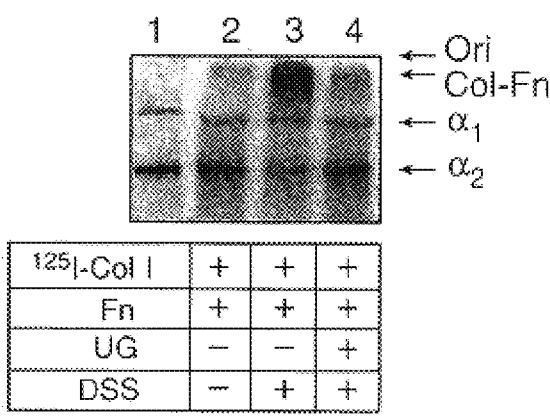

To determine whether there is any difference between the binding affinities of Fn for UG and that of Fn for itself binding experiments were performed in which $^{125}$I-Fn was incubated with unlabeled Fn and immobilized on multiwell plates together with varying concentrations of UG. In separate experiments, binding studies of $^{125}$I-Fn with unlabeled, immobilized Fn using various concentrations of unlabeled soluble Fn, were also done. The Scatchard analyses of the data from both types of binding experiments yielded straight lines with Kds of 13 nM for UG binding to Fn and 176 nM for Fn binding to itself. These results suggest that, due to a relatively higher binding-affinity of UG for Fn, UG may effectively counteract Fn self-aggregation. Affinity-crosslinking experiments in which radio-iodinated ($^{125}$I)-collagen I was incubated with unlabeled Fn in the absence or presence of UG, were also done as described above for Fn. Fifteen µl of either denatured or non-denatured $^{125}$I-collagen I (Sp. Act. 65.4 mCi/mg) were incubated with Fn in presence or absence of reduced UG (250 µg), affinity crosslinked, electrophoresed and autoradiographed. The results indicate that UG counteracts the formation of high molecular weight $^{125}$I-collagen-Fn aggregates (FIG. 5F).

Example 11
In vivo Inhibition of Glomerular Fn Deposition by UG

To test whether UG protects the renal glomeruli from Fn accumulation, soluble human Fn (hFn) alone, or hFn mixed with equimolar concentrations of UG, was administered intravenously to UG$^{+/+}$ and to apparently healthy UG$^{-/-}$ littermates. Human Fn (500 µg/150 µl PBS) was administered in the tail vein of two-month old, approximately 22 g, UG$^{+/+}$ and apparently healthy, UG$^{-/-}$ mice. Similarly, the control mice were injected with a mixture of 500 µg of hFn either with equimolar concentrations of UG or albumin in 150 µl PBS. Twenty-four hours after the last injection, the mice were sacrificed and various organs were fixed in buffered formalin. The histological sections of the kidneys and other organs were examined by immunofluorescence (Peri, A., Cordella-Miele, E., Miele, L., and A. B. Mukheljee, J Clin. Invest. 92: 2099 (1993); Peri, A, Dubin, N., Dhanireddy, R., and A. B. Mukherjee, J Clin. Invest. 96: 343 (1995)) with a monospecific hFn antibody (GIBCO BRL; clone 1) and FITC conjugated rabbit anti-mouse IgG (Cappel). In a separate experiment, UG$^{+/+}$ mice were injected with 1 mg of Fn alone in 150 µl PBS daily for 3 consecutive days.

The rationale for injecting human Fn was to be able to discriminate between endogenous murine Fn and the administered hFn. The method of intravenous administration and immunohistochemical detection of hFn in various tissues have been described (E. Oh, M. Pierschbacher and E. Ruoslahti, Proc. Natl. Acad. Sci. (USA) 78, 3218 (1981)).

Human Fn immunofluorescence in the glomeruli of wild-type UG$^{+/+}$ mice injected with either a mixture of hFn and UG (1:1 molar ratio) or with hFn alone was similar (FIGS. 6A and 6B). However, the UG$^{-/-}$ mice injected with a mixture of hFn and UG showed little hFn-specific immunofluorescence in the glomeruli (FIG. 6C), while those receiving Fn alone exhibited higher intensity immunofluorescence (FIG. 6D). Administration of a mixture of hFn and BSA, as a control, yielded no protective effect.

To determine whether this UG protective effect could be overcome by injecting larger quantities of Fn in UG$^{+/+}$ mice, we injected 1 mg of hFn per animal daily for three consecutive days (E. Oh, M. Pierschbacher and E. Ruoslahti, Proc. Natl. Acad. Sci. (USA) 78, 3218 (1981)). Although intravenous administration of hFn to UG$^{+/+}$ mice at lower doses (500 µg/animal) was not effective in causing any appreciable glomerular deposition (FIG. 6A), the administration of higher doses (3 mg/animal) led to a significant accumulation (Zhang, Z. et al. unpublished results). Thus, UG prevents glomerular Fn-deposition, and UG$^{+/+}$ as opposed to UG$^{-/-}$ mice have a higher threshold for the accumulation of soluble Fn, due to the presence of endogenous UG.

Example 12
Inhibition of Fibrilogenesis and Fn Matrix Aassembly by UG in Tissue Culture Cells To determine whether UG prevents Fn-fibrilogenesis and matrix assembly in a typical in vitro tissue culture assay, mouse embryonic fibroblasts were cultured in medium containing either soluble hFn alone or a mixture of equimolar concentrations of hFn and UG. Fn matrix assembly and fibrilogenesis in cultured cells (CRL6336, ATCC) were determined as described (D.F.Mosher, J, Sottile, C. Wu and J. A. McDonald, Curr. Biol. 4, 810 (1992)). The level of fibrilogenesis seen in the cells of cultures treated with hFn alone was much higher (FIG. 6E) compared to those which received a mixture of hFn and UG (FIG. 6F).

Example 13
Detection of UG-Fn Complexes in Clinical Samples.

Figure 7A:
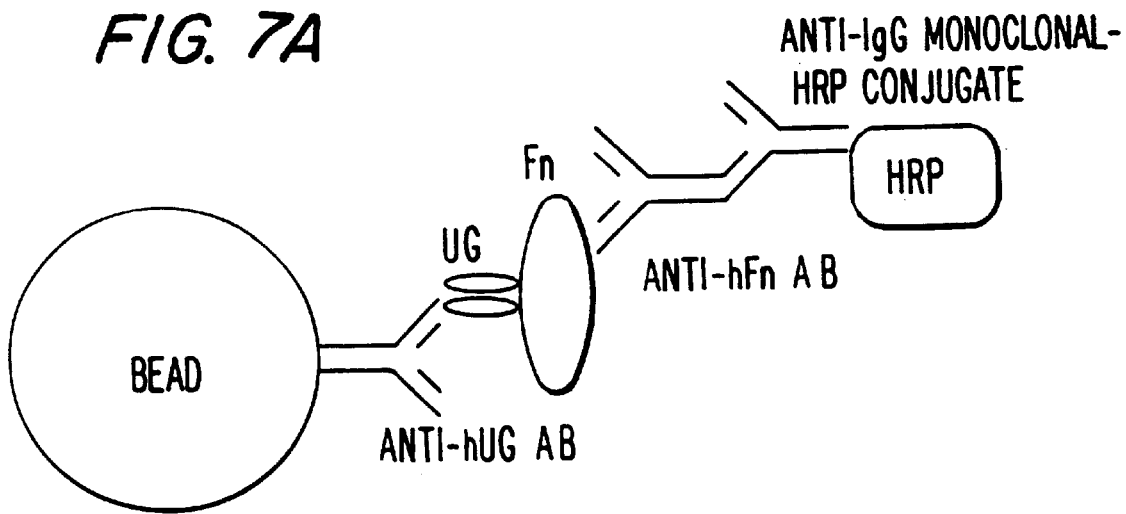
FIGS. 7A–7B show the format for a diagnostic assay to detect UG-Fn complexes in clinical samples.
Figure 7B:
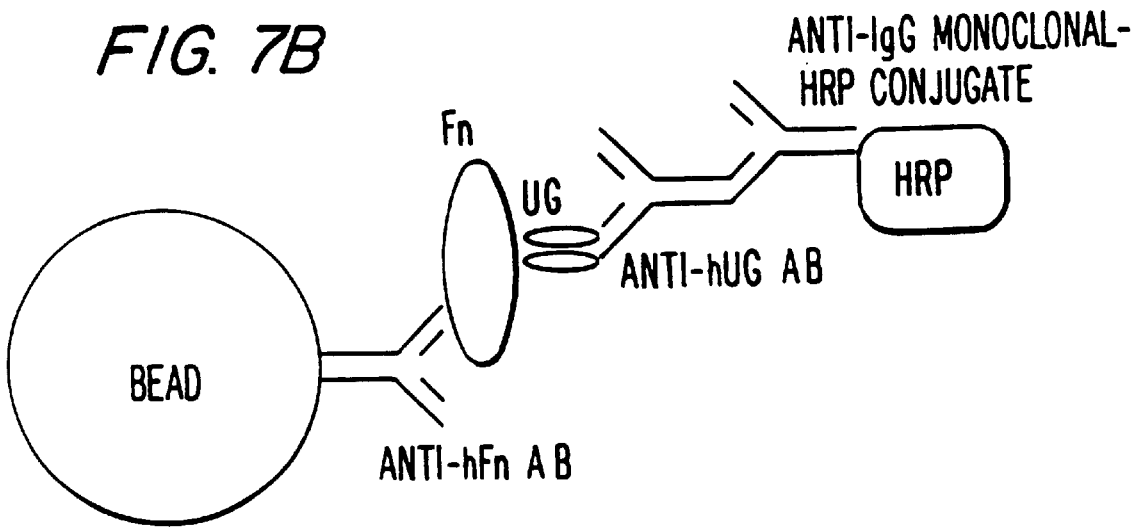

Detection of UG-Fn complexes in clinical samples of bodily fluids such as serum, BAL fluids, and sputum is important in defining the role of this complex in human disease. A solution phase diagnostic assay for the detection of UG-Fn complexes is developed and the assay format is shown in FIG. 7. The capture antibody, covalently linked to a solid support, is a monospecific rabbit polyclonal raised against the human protein (A. B. Mukherjee, laboratory reagent). The solid support may be a bead, such as a magnetic bead, a tube, or an ELISA plate. The solid support affords the flexibility of performing wash steps after each binding reaction in order to obtain more consistent results with a variety of sample types. The detection antibody is specific for Fn, and available from a number of commercial sources. An anti-IgG antibody, conjugated to an enzyme such as horse radish peroxidase (HRP), is then used to detect the anti-Fn IgG at the end of the molecular chain in a standard enzymatic reaction in which the enzyme substrate is converted to a chromogenic or fluorogenic compound that is quantitated with a spectrophotometer or fluorimeter (Amersham). The detection limit for this assay is 500 µg of UG-Fn complex per ml of sample fluid.

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims.

What is claimed is:

1. A method for inhibiting fibronectin-fibronectin binding and/or fibronectin deposition comprising exposing the fibronectin to recombinant human uteroglobin (rhUG) wherein the rhUG binds the fibronectin and inhibits fibronectin-fibronectin binding and/or fibronectin deposition.

2. The method of claim 1, wherein fibronectin self-assembly, formation of collagen-fibronectin aggregates, fibronectin accumulation, or fibrillogenesis is inhibited.

3. The method of claim 1, wherein the rhUG is administered to a patient and fibronectin self-assembly, formation of collagen-fibronectin aggregates, fibronectin accumulation, or fibrillogenesis is inhibited.

4. Method according to claim 3, wherein said rhUG is administered in an amount of a single bolus of 20 ng/kg to 500 mg/kg, in a single dose or in multiple doses of said single bolus, or as a continuous infusion of up to 10 grams.

5. Method according to claim 3, wherein said rhUG is administered in a composition comprising a lung surfactant.

6. Method according to claim 3, wherein said rhUG is administered by injection.

7. Method according to claim 3, wherein said rhUG is administered as a semi-aerosol via an intratracheal tube.

8. The method of claim 3, wherein the patient is afflicted with or at risk of a fibrotic condition.

9. The method of claim 8, wherein the fibrotic condition is characterized by a deficiency of endogenous uteroglobin (UG).

10. The method of claim 8, wherein said fibrotic condition is pulmonary fibrosis or renal fibrosis.

* * * * *

SEQUENCE LISTING

<160> NUMBER OF SEQ ID NOS: 22

<210> SEQ ID NO: 1
<211> LENGTH: 70
<212> TYPE: PRT
<213> ORGANISM: human

<400> SEQUENCE: 1

Glu Ile Cys Pro Ser Phe Gln Arg Val Ile Glu Thr Leu Leu Met Asp
1               5                   10                  15

Thr Pro Ser Ser Tyr Glu Ala Ala Met Glu Leu Phe Ser Pro Asp Gln
                20                  25                  30

Asp Met Arg Glu Ala Gly Ala Gln Leu Lys Lys Leu Val Asp Thr Leu
            35                  40                  45

Pro Gln Lys Pro Arg Glu Ser Ile Ile Lys Leu Met Glu Lys Ile Ala
        50                  55                  60

Gln Ser Ser Leu Cys Asn
65              70

<210> SEQ ID NO: 2
<211> LENGTH: 69
<212> TYPE: PRT
<213> ORGANISM: rabbit

<400> SEQUENCE: 2

Gly Ile Cys Pro Arg Phe Ala His Val Ile Glu Asn Leu Leu Leu Gly
1               5                   10                  15

Thr Pro Ser Ser Tyr Glu Thr Ser Leu Lys Glu Phe Glu Pro Asp Asp
                20                  25                  30

Thr Met Lys Asp Ala Gly Met Gln Met Lys Lys Val Leu Asp Ser Leu
            35                  40                  45

Pro Gln Thr Thr Arg Glu Asn Ile Met Lys Leu Thr Glu Lys Ile Val
        50                  55                  60

Lys Ser Pro Leu Cys
65

<210> SEQ ID NO: 3
<211> LENGTH: 75
<212> TYPE: PRT
<213> ORGANISM: rat

<400> SEQUENCE: 3

Asp Ile Cys Pro Gly Phe Leu Gln Val Leu Glu Ala Leu Leu Leu Gly
1               5                   10                  15

Ser Glu Ser Asn Tyr Glu Ala Ala Leu Lys Pro Phe Asn Pro Ala Ser
                20                  25                  30

```
Asp Leu Gln Asn Ala Gly Thr Gln Leu Lys Arg Leu Val Asp Thr Leu
            35                  40                  45

Pro Gln Glu Thr Arg Ile Asn Ile Val Lys Leu Thr Glu Lys Ile Leu
        50                  55                  60

Thr Ser Pro Leu Cys Glu Gln Asp Leu Arg Val
 65                 70                  75

<210> SEQ ID NO: 4
<211> LENGTH: 75
<212> TYPE: PRT
<213> ORGANISM: mouse

<400> SEQUENCE: 4

Asp Ile Cys Pro Gly Phe Leu Gln Val Leu Glu Ala Leu Leu Met Glu
 1               5                  10                  15

Ser Glu Ser Gly Tyr Val Ala Ser Leu Lys Pro Phe Asn Pro Gly Ser
            20                  25                  30

Asp Leu Gln Asn Ala Gly Thr Gln Leu Lys Arg Leu Val Asp Thr Leu
            35                  40                  45

Pro Gln Glu Thr Arg Ile Asn Ile Met Lys Leu Thr Glu Lys Ile Leu
        50                  55                  60

Thr Ser Pro Leu Cys Lys Gln Asp Leu Arg Phe
 65                 70                  75

<210> SEQ ID NO: 5
<211> LENGTH: 3
<212> TYPE: PRT
<213> ORGANISM: artificial
<220> FEATURE:
<223> OTHER INFORMATION: primer sequence

<400> SEQUENCE: 5

Met Ala Ala
 1

<210> SEQ ID NO: 6
<211> LENGTH: 65
<212> TYPE: DNA
<213> ORGANISM: artificial
<220> FEATURE:
<223> OTHER INFORMATION: primer sequence

<400> SEQUENCE: 6
gatccatgga aatctgcccg tctttccagc gtgttatcga aaccctgctg atggacaccc      60
cgtcc                                                                 65

<210> SEQ ID NO: 7
<211> LENGTH: 60
<212> TYPE: DNA
<213> ORGANISM: artificial
<220> FEATURE:
<223> OTHER INFORMATION: primer sequence

<400> SEQUENCE: 7
agctacgaag cagctatgga actgttctct ccggaccagg acatgcgtga agcaggtgct      60

<210> SEQ ID NO: 8
<211> LENGTH: 59
<212> TYPE: DNA
<213> ORGANISM: artificial
<220> FEATURE:
<223> OTHER INFORMATION: primer sequence
```

<400> SEQUENCE: 8
cagctgaaga aactggttga caccctgccg cagaaaccgc gtgaatccat cataaactg      59

<210> SEQ ID NO: 9
<211> LENGTH: 37
<212> TYPE: DNA
<213> ORGANISM: artificial
<220> FEATURE:
<223> OTHER INFORMATION: primer sequence

<400> SEQUENCE: 9
atggagaaga tcgctcagtc tagcctgtgc aactaag                              37

<210> SEQ ID NO: 10
<211> LENGTH: 60
<212> TYPE: DNA
<213> ORGANISM: artificial
<220> FEATURE:
<223> OTHER INFORMATION: primer sequence

<400> SEQUENCE: 10
cttagttgca caggctagac tgagcgatct tctccatcag tttgatgatg gattcacgcg     60

<210> SEQ ID NO: 11
<211> LENGTH: 59
<212> TYPE: DNA
<213> ORGANISM: artificial
<220> FEATURE:
<223> OTHER INFORMATION: primer sequence

<400> SEQUENCE: 11
gtttctgcgg cagggtgtca accagtttct tcagctgagc actgcttcac gcatgtcct     59

<210> SEQ ID NO: 12
<211> LENGTH: 60
<212> TYPE: DNA
<213> ORGANISM: artificial
<220> FEATURE:
<223> OTHER INFORMATION: primer sequence

<400> SEQUENCE: 12
ggtccggaga gaacagttcc atagctgctt cgtagctgga cggggtgtcc atcagcaggg     60

<210> SEQ ID NO: 13
<211> LENGTH: 42
<212> TYPE: DNA
<213> ORGANISM: artificial
<220> FEATURE:
<223> OTHER INFORMATION: primer sequence

<400> SEQUENCE: 13
tttcgataac acgctggaaa gacgggcaga tttccatgga tc                        42

<210> SEQ ID NO: 14
<211> LENGTH: 23
<212> TYPE: DNA
<213> ORGANISM: artificial
<220> FEATURE:
<223> OTHER INFORMATION: primer-L

<400> SEQUENCE: 14
ttccaaggca gaacatttga gac                                             23

<210> SEQ ID NO: 15
<211> LENGTH: 21

```
<212> TYPE: DNA
<213> ORGANISM: artificial
<220> FEATURE:
<223> OTHER INFORMATION: primer-R

<400> SEQUENCE: 15
tctgagccag ggttgaaagg c                                              21

<210> SEQ ID NO: 16
<211> LENGTH: 23
<212> TYPE: DNA
<213> ORGANISM: artificial
<220> FEATURE:
<223> OTHER INFORMATION: mPr primer sequence

<400> SEQUENCE: 16
atcttgctta cacagaggac ttg                                            23

<210> SEQ ID NO: 17
<211> LENGTH: 20
<212> TYPE: DNA
<213> ORGANISM: artificial
<220> FEATURE:
<223> OTHER INFORMATION: mPl primer sequence

<400> SEQUENCE: 17
atcgccatca caatcactgt                                                20

<210> SEQ ID NO: 18
<211> LENGTH: 25
<212> TYPE: DNA
<213> ORGANISM: artificial
<220> FEATURE:
<223> OTHER INFORMATION: mPp primer sequence

<400> SEQUENCE: 18
atcagagtct ggttatgtgg catcc                                          25

<210> SEQ ID NO: 19
<211> LENGTH: 20
<212> TYPE: DNA
<213> ORGANISM: artificial
<220> FEATURE:
<223> OTHER INFORMATION: mGAPDH-r primer sequence

<400> SEQUENCE: 19
ggcatcgaag gtggaagagt                                                20

<210> SEQ ID NO: 20
<211> LENGTH: 20
<212> TYPE: DNA
<213> ORGANISM: artificial
<220> FEATURE:
<223> OTHER INFORMATION: mGAPDH-1 probe sequence

<400> SEQUENCE: 20
atggccttcc gtgttcctac                                                20

<210> SEQ ID NO: 21
<211> LENGTH: 26
<212> TYPE: DNA
<213> ORGANISM: artificial
<220> FEATURE:
<223> OTHER INFORMATION: mGAPDH-p probe sequence

<400> SEQUENCE: 21
```

```
gaaggtggtg aagcaggcat ctgagg                                              26

<210> SEQ ID NO: 22
<211> LENGTH: 22
<212> TYPE: PRT
<213> ORGANISM: mouse

<400> SEQUENCE: 22

Lys Pro Phe Asn Pro Gly Ser Asp Leu Gln Asn Ala Gly Thr Gln Leu
1               5                   10                  15

Lys Arg Leu Val Asp Thr
            20
```